US009181531B2

(12) United States Patent
Arhancet et al.

(10) Patent No.: US 9,181,531 B2
(45) Date of Patent: *Nov. 10, 2015

(54) PROCESS FOR PURIFYING VLPS

(71) Applicant: APSE, LLC, St. Louis, MO (US)

(72) Inventors: Juan Pedro Humberto Arhancet, Creve Coeur, MO (US); Juan P. Arhancet, Creve Coeur, MO (US); Kimberly Delaney, St. Louis, MO (US); Kathleen B. Hall, St. Louis, MO (US); Neena Summers, St. Charles, MO (US)

(73) Assignee: APSE, LLC, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/279,793

(22) Filed: May 16, 2014

(65) Prior Publication Data

US 2014/0302593 A1 Oct. 9, 2014

Related U.S. Application Data

(63) Continuation of application No. 13/725,184, filed on Dec. 21, 2012.

(60) Provisional application No. 61/607,900, filed on Mar. 7, 2012, provisional application No. 61/578,706, filed on Dec. 21, 2011, provisional application No. 61/661,688, filed on Jun. 19, 2012.

(51) Int. Cl.
*C12N 7/01* (2006.01)
*C12N 15/113* (2010.01)
*C12N 7/04* (2006.01)
*C07K 14/01* (2006.01)
*C12N 7/00* (2006.01)
*A01N 25/26* (2006.01)
*A01N 25/28* (2006.01)
*C12N 15/11* (2006.01)
*C07K 14/005* (2006.01)

(52) U.S. Cl.
CPC *C12N 7/00* (2013.01); *A01N 25/26* (2013.01); *A01N 25/28* (2013.01); *C07K 14/005* (2013.01); *C07K 14/01* (2013.01); *C12N 7/04* (2013.01); *C12N 15/111* (2013.01); *C12N 15/113* (2013.01); *C12N 2310/121* (2013.01); *C12N 2310/123* (2013.01); *C12N 2310/128* (2013.01); *C12N 2310/14* (2013.01); *C12N 2310/16* (2013.01); *C12N 2330/51* (2013.01); *C12N 2795/18122* (2013.01); *C12N 2795/18123* (2013.01); *C12N 2795/18142* (2013.01)

(58) Field of Classification Search
None
See application file for complete search history.

(56) References Cited

U.S. PATENT DOCUMENTS

| | | | |
|---|---|---|---|
| 5,443,969 A | 8/1995 | Wilson et al. | |
| 6,066,318 A | 5/2000 | Feng et al. | |
| 6,932,971 B2* | 8/2005 | Bachmann et al. | 424/193.1 |
| 2003/0099668 A1 | 5/2003 | Bachmann et al. | |
| 2004/0171115 A1 | 9/2004 | Feng et al. | |
| 2005/0260758 A1 | 11/2005 | Rasochova et al. | |
| 2006/0177819 A1 | 8/2006 | Smith et al. | |
| 2008/0171361 A1 | 7/2008 | Scheets et al. | |
| 2008/0312176 A1 | 12/2008 | Baulcombe et al. | |
| 2009/0093019 A1* | 4/2009 | Phelps et al. | 435/69.1 |
| 2010/0167981 A1* | 7/2010 | Bundy et al. | 514/2 |
| 2011/0250675 A1 | 10/2011 | Bennett | |
| 2011/0296556 A1 | 12/2011 | Sammons et al. | |
| 2012/0064169 A1 | 3/2012 | Cheng et al. | |
| 2012/0174263 A1 | 7/2012 | Saunders et al. | |
| 2012/0301494 A1 | 11/2012 | Cheng et al. | |
| 2013/0167267 A1 | 6/2013 | Arhancet et al. | |

FOREIGN PATENT DOCUMENTS

| | | |
|---|---|---|
| WO | 02056905 A2 | 7/2002 |
| WO | 2009095791 A1 | 8/2009 |
| WO | 2012051152 A2 | 4/2012 |
| WO | 2012061445 A2 | 5/2012 |
| WO | 2013096866 A2 | 6/2013 |

OTHER PUBLICATIONS

Wigginton et al. (Environ. Sci. Technol., 44, pp. 5437-5443, 2010).*
Nasser et al. (Water Research, 36, pp. 2589-2595, 2002).*
Pecson et al (Applied and Environmental Microbiology, 75(17), pp. 5544-5554, 2009).*
Marin (Eur. J. Biochem., 151, pp. 131-140, 1985).*
Kawasaki et al., (Differentiation, 72, pp. 58-64, 2004).*
International Search Report and Written Opinion regarding PCT/US2012/071419, dated Jul. 22, 2013, 22 pages.
Rhee, J.K. et al, Colorrful Virus-Like Particles: Flourescent Protein Packaging by the Qbeta Capsid, Biomacromolecules, 2011, pp. 3977-3981, vol. 12, No. 11.
Beams, B. and Lanford, R.E., Insertions within the Hepatitis B Virus Capsid Protein Influence Capsid Formation and RNA Encapsidation, J. Virology, 1995, pp. 6833-6838, vol. 69, No. 11.
Been, M.D. and Perrotta, A.T., Optimal self-cleavage activity of the hepatitis delta virus RNA is dependent on a homopurine base pair in the ribozyme core, RNA, 1995, pp. 1061-1070, vol. 1.
Li, T.C. et al, Essential Elements of the Capsid Protein for Self-Assembly into Empty Virus-Like Particles of Hepatitis E Virus, J. Virology, 2005, pp. 12999-13006, vol. 79, No. 20.
Morgenstern, B. et al, Multiple sequence alignment with user-defined anchor points, Algorithms for Molecular Biology, 2006, p. 1-12, vol. 1, No. 6.

(Continued)

*Primary Examiner* — David T Fox
*Assistant Examiner* — Stephen Uyeno
(74) *Attorney, Agent, or Firm* — Morgan, Lewis & Bockius LLP

(57) ABSTRACT

Processes and compositions to produce, package, and purify virus like particles containing heterologous cargo molecules utilizing self assembling proteins and protease treatment coupled with simple precipitation and filtration methods are described.

19 Claims, 16 Drawing Sheets

(56) References Cited

OTHER PUBLICATIONS

Patkar, C.G. et al, Functional Requirements of the Yellow Fever Virus Capsid Protein, J. Virology, 2007, pp. 6471-6481, vol. 81, No. 12.

Zlotnick, A. et al, Localization of the C terminus of the assembly domain of hepatitis B virus capsid protein: Implications for morphogenesis and organization of encapsidated RNA, PNAS, 1997, pp. 9556-9561, vol. 94.

Agbottah, E. et al, Antiviral Activity of CYC202 in HIV-1-infected Cells, J. Biol. Chem, 2005, pp. 3029-3042, vol. 280, No. 4.

Askonas B.A., The Use of Organic Solvents at Low Temperature for the Separation of Enzymes. Application to Aqueous Rabbit Muscle Extract, Biochemical J., 1951, pp. 42-48, vol. 48.

Benson, D.A., et al, GenBank, Nucleic Acids Res., 2005, pp. D34-D38, vol. 33.

Cellitti, S.E. et al, In vivo incorporation of unnatural amino acids to probe structure, dynamics and ligand binding in a large protein by Nuclear Magnetic Resonance spectroscopy, J. Am. Chem. Soc., 2008, pp. 9268-9281, vol. 130, No. 29.

Chang, J.R. et al, Incorporation of scaffolding protein gpO in bacteriophages P2 and P4, Virology, 2008, pp. 352361-vol. 370, No. 2.

Cheng, Y. et al, Preparation of His-Tagged Armored RNA Phage Particles as a Control for Real-Tie Reverse Transcription-PCR Detection of Severe Acute Respiratory Syndrome Coronavirus, J. Clinical Microbiology, 2006, pp. 3557-3561, vol. 44, No. 10.

Chothia, C. and Lesk, A.M., The relation between the divergence of sequence4 and structure in proteins, EMBO J., 1986, pp. 823-826, vol. 5, No. 4.

Clark, S.M. et al, Trypsin enhancement of rotavirus infectivity: mechanism of enhancement, J. Virology, 1981, pp. 816-822, vol. 39, No. 3.

Davis, M.E. et al, Evidence of RNAi in humans from systemically administered siRNA via targeted nanoparticles, Nature, 2010, pp. 1067-1070, vol. 464, No. 7291.

Draghi, J.A. et al, Mutational robustness can facilitate adaptation, Nature, 2010, pp. 353-355, vol. 463, No. 7279.

Ferre-Damare, A.R. and Doudna, J.A., Use of cis- and trans-ribozymes to remove 5' and 3' heterogeneities from milligrams of in vitro transcribed RNA, Nucleic Acids Res., 1996, pp. 977-978, vol. 24, No. 5.

Fiedler, J.D. et al, RNA-Directed Packaging of Enzymes within Virus-Like Particles, Angew Chem Int Ed Engl, 2010, pp. 9648-9651, vol. 49, No. 50.

Gailus, V. and Rasched, I., The adsorption protein of bacteriophage fd and its neighbour minor coat protein build a structural entity, Eur. J. Biochem., 1994, pp. 927-931, vol. 222.

uniprot.org website, Welcome page: Resource of protein sequence and functional information, http://www.uniprot.org, Jan. 15, 2013, one page.

rcsb.org website, RCSB PDB Protein Comparision Tool, http://www.rcsb.or/pdb/workbench/workbench.do, one page.

rcsb.org website, RCSB information Portal to Biological Macromolecular Structures, http://www.rcsb.org/pdb/home/home.do, two pages.

Jegerlehner, A. et al, TLR9 Signaling in B Cells Determines Class Switch Recombination to IgG2a, J. of Immunology, 2007, pp. 2415-2420, vol. 178.

Karlin, S. and Altschul, S.F., Methods for assessing the statistical significance of molecular sequence features by using general scoring schemes, PNAS, 1990, pp. 2264-2268, vol. 87.

Lee, J.H. et al, Receptor mediated uptake of peptides that bind the human transferrin receptor, Eur. J. Biochem., 2001, pp. 2004-2012, vol. 268.

Maruyama, I.N., Maruyama, H.I. and Brenner, S., λfoo: A λ phage vector for the expression of foreign proteins, PNAS, 1994, pp. 8273-8277, vol. 91.

Olins, P.O. et al, Saturation Mutagenesis of Human Interleukin-3*, J. Biol. Chem., 1995, pp. 23754-23760, vol. 270, No. 40.

Paige, J.S., Wu, K. and Jaffrey, S.R., RNA mimics of green fluorescent protein, Science, 2011, pp. 642-646, vol. 333, No. 6042.

Peabody, D.S. et al, Immunogenic Display of Diverse Peptides on Virus-Like Particles of RNA Phage MS2, J. Mol. Biol., 2008, pp. 252-263, vol. 380, No. 1.

Pearson, W.R. and Lipman, D.J., Improved tools for biological sequence comparison, PNAS, 1988, pp. 2444-2448, vol. 85.

Petruzziello, R. et al, Pathway of rubella virus infections entry into Vero cells, J. Gen. Virology, 1996, pp. 303-308, vol. 77.

Pickett, G.G. and Peabody, D.S., Encapsidation of heterologous RNAs by bacteriophage MS2 coat protein, Nucleic Acids Research, 1993, pp. 4621-4626, vol. 21, No. 19.

Plevka, P., Tars, K. and Liljas, L., Crystal packing of a bacteriophage MS2 coat protein mutant corresponds to octahedral particles, Protein Science, 2008, pp. 1731-1739, vol. 17.

Prlic, A., et al, Pre-calculated protein structure alignments at the RCSB PDB website, Bioinformatics, 2010, pp. 2983-2985, vol. 26, No. 23.

Sanjuan, R. et al, Viral Mutation Rates, J. Virology, 2010, pp. 9733-9748, vol. 84, No. 19.

Schwind, P. et al, Subtilisin removes the surface layer of the phage fd coat, Eur. J. Biochem, 1992, pp. 431-436, vol. 210.

Simon, L.D. et al, Stabilization of proteins by a bacteriophage T4 gene cloned in *Escherichia coli*, PNAS, 1983, pp. 2059-2062, vol. 80.

Sinha, J., Reyes, S.J. and Gallivan, J.P., Reprogramming Bacteria to Seek and Destroy a Herbicide, Nat Chem Biol., 2010, pp. 464-470, vol. 6, No. 6.

Song, H., Chen, D.L. and Ismagilov, R.F., Angew Chem Int Ed Engl., 2006, pp. 7336-7356, vol. 45, No. 44.

The Uniport Consortium, Reorganizing the protein space at the Universal Protein Resource, Nucleic Acids Research, 2012, pp. D71-D75, vol. 40, Database issue.

Van Den Worm, S. H. E., et al, Crystal structures of MS2 coat protein mutants in complex with wild-type RNA operator fragments, Nucleic Acids Research, 1998, pp. 1345-1351, vol. 26, No. 5.

Walton, S. P. et al, Designing Highly Active siRNAs for Therapeutic Applications, FEBS J., 2010, pp. 4806-4813, vol. 277, No. 23.

Worsdorfer, B. et al, Directed Evolution of a Protein Container, Science, 2011, pp. 589-592, vol. 331.

Wei, Y. et al, RNase-Resistant Virus-Like Particles Containing Long Chimeric RNA Sequences Produced by Two-Plasmid Coexpression System, J. Clinical Microbiology, 2008, pp. 1734-1740, vol. 46, No. 5.

Wimmer, E. et al, Synthetic viruses: a new opportunity to understand and prevent viral disease, Nat Biotechnol, 2009, pp. 1163-1172, vol. 27, No. 12.

Altschul, S.F. et al, Basic Local Alignment Search Tool, J. Mol. Biol., 1990, pp. 403-410, vol. 215.

Ayuso-Tejedor, S. et al, Underexposed polar residues and protein stabilization, PEDS, 2010, pp. 1-7.

Brustad, E. et al, A Genetically Encoded Boronate-Containing Amino Acid, Angew. Chem., 2008, pp. 8344-8347, vol. 120.

Burster, T. et al, Design of protease-resistant myelin basic protein-derived peptides by cleavage site directed amino acid substitutions, Biochemical Pharmacology, 2007, pp. 1514-1523, vol. 74.

Carr, P.A. and Church, G.M., Genome engineering, Nature Biotechnology Review, 2009, pp. 1151-1162, vol. 27, No. 12.

Chomczynski, P. and Sacchi, N., The single-step method of RNA isolation by acid guanidinium thiocyanate-phenol-chloroform extraction: twenty-something years on, Nature Protocols, 2006, pp. 581-585, vol. 1., No. 2.

Chothia, C. et al, Domain Association in Immunoglobulin Molecules the Packing of Variable Domains, J. Mol Biol., 1985, pp. 651-663, vol. 186.

Feng, Y, Klein B.K. and McWherter, C.A., Three-dimensional Solution Structure and Backbone Dynamics of a Variant of Human Interleukin-3, J. Mol. Biol., 1996, pp. 524-541, vol. 259.

Ferre-D'Amare, A.R. and Scott, W.G., Small Self-cleaving Ribozymes, Cold Spring Harbor Perspectives in Biology, http://cshperspectives.schlp.org, published Sep. 15, 2010, pp. 11.

Fischlechner, M. and Donath, E., Viruses as Building Blocks for Materials and Devices, Angew. Chem. Int. Ed., 2007, ppl 3184-3193, vol. 46.

(56) References Cited

OTHER PUBLICATIONS

Fraczkiewicz, R. and Braun, W., Exact and Efficient Analytical Calculation of the Accessible Surface Areas and Their Gradients for Macromolecules, J. Computational Chemistry, 1998, pp. 319-333, vol. 19, No. 3.
Gottschalk, U., Bioseparation in Antibody Manufacturing: The Good, the Bad and the Ugly, Biotechnol. Prog., 2008, pp. 496-503, vol. 24.
Hammill, J.T. et al, Preparation of site-specifically labeled fluorinated proteins for 19F-NMR structural characterization, Nature Protocols, 2007, pp. 2601-2607, vol. 2, No. 10.
Haussecker, D., The Business of RNAi Therapeutics, Human Gene Therapy, 2008, pp. 451-462, vol. 19.
Johnson, H.R. et al, Solubilization and Stabilization of Bacteriophage MS2 in Organic Solvents, Biotechnology and Bioengineering, 2007, pp. 224-234, vol. 97, No. 2.
Jung, S. et al, Limited Hydrolysis of Soy Proteins with Endo- and Exoproteases, JAOCS, 2004, pp. 953-960, vol. 81, No. 10.
Kamtekar, S. et al, Protein Design by Binary Patterning of Polar and Nonpolar Amino Acids, Science, 1993, pp. 1680-1685, vol. 262.
Kastelein, R.A. et al, Lysis gene expression of RNA phage MS2 depends on a frameshift during translation of the overlapping coat protein gene, Nature, 1982, pp. 35-41, vol. 295.
Kelley, B.. Very Large Scale Monoclonal Antibody Purification: The Case for Conventional Unit Operations, Biotechnol Prog, 2007, pp. 995-1008, vol. 23.
Kleywegt, G.J. and Jones, T. A., Phi/Psi-chology: Ramachandran revisited, Structure, 1996, pp. 1395-1400, vol. 4.
Legendre, D. and Fastrez, J., Production in Saccharomyces cerevisiae of MS2 virus-like particles packaging funct8ional heterologous mRNAs, J. Biotechnology, 2005, pp. 183-194, vol. 117.
Lesur, A., Varesio, E. and Hopfgartner, G., Accelerated tryptic digestion for the analysis of biopharmaceutical monoclonal antibodies in plasma by liquid chromatography with tandem mass spectrometric detection, J. of Chromoatography A., 2010, pp. 57-64, vol. 1217.
Li, H., Chen, S. and Zhao, H., Fat fractal and multifractals for protein and enzyme surfaces, Int. J. Biol. Macromol., 1991, pp. 210-2016, vol. 13.
Liljas, L. et al, Crystal Structure of Bacteriophage fr Capsids at 3.5 Å Resolution, J. Mol. Biol., 2994, pp. 279-290, vol. 244.
Low, D., Oleary, R. and Pujar, N.S., Future of antibody purification, J. of Chromatography B., 2007, pp. 48-63, vol. 848.
Marsh, E.N.G., Buer, B.C. and Ramamoorthy, A., Fluorine—a new element in the design of membrane-active peptides, Mol. BioSyst., 2009, pp. 1143-1147, vol. 5.
Matlin, K.S. et al, Pathway of Vesicular Stomatitis Virus Entry Leading to Infection, J. Mol. Biol., 1982, pp. 609-631, vol. 156.
Mazzola, P.G. et al, Review: Liquid-liquid extraction of biomolecules: an overview and update of the main techniques, J. Chem. Technol. Biotechnol, 2008, pp. 143-157, vol. 83.
Micura, R., Small Interfering RNAs and Their Chemical Synthesis, Angew. Chem. Int. Ed., 2002, pp. 2265-2269, vol. 41, No. 13.
Miyaura, N. and Suzuki, A., Palladium-Catalyzed Cross-Coupling Reactions of Organoboron Compounds, Chem. Rev., 1995, pp. 2457-2483, vol. 95.
Murzin, A.G., Structural classification of proteins: new superfamilies, Curr Opin Struct Biol, 1996, pp. 386-394, vol. 6.
Nelson, A.L., Dhimolea, E. and Reichert, J.M., Development trends for human monoclonal antibody therapeutics, Nature Reviews-Drug Discovery, 2010, pp. 767-774, vol. 9.
Ochoa, W., et al, Generation and Structural Analysis of Reactive Empty Particles Derived from an Icosahedral Virus, Chemistry and Biology, 2006, pp. 771-778, vol. 13.
Pattenden, L.K. et al, Towards the preparative and large-scale precision manufacture of virus-like particles, TRENDS Biotechnology, 2005, pp. 523-529, vol. 23.
Pettersen, E.F. et al, UCSF Chimera—A Visualization System for Exploratory Research and Analysis, J. Comput Chem, 2004, pp. 1605-1612, vol. 25.
Przybycien, T.M., Pujar, N.S. and Steele, L.M., Alternative bioseparation operations: life beyond packed-bed chromatography, Current Opinion in Biotechnology, 2004, pp. 469-478, vol. 15.
Rennell, D. et al, Systematic Mutation of Bacteriophage T4 Lysozyme, J. Mol. Biol., 1991, pp. 67-87, vol. 222.
Rohrmann, G.F. and Krueger, R.G., Physical, Biochemical, and Immunological Properties of Coliphage MS-2 Particles, J. Virol., 1970, pp. 269-279, vol. 6, No. 3.
Sieber, V., Pluckthun, A. and Schmid, F.X., Selecting proteins with improved stability by a phage-based method, Nature Biotechnology, 1998, pp. 955-960, vol. 16.
Sett, A. et al, Aptasensors in Health, Environment and Food Safety Monitoring, Open J. Applied Biosensor, 2012, pp. 9-19, vol. 1.
Shenton, W., et al, Synthesis of Nanophase Iron Oxide in Lumazine Synthase Capsids, Angew. Chem. Int. Ed., 2001, pp. 442-445, vol. 40, No. 2.
Sousa, R., Patra, D. and Lafer, E.M., Model for the Mechanism of Bacteriophage T7 RNAP Transcription Initiation and Termination, J. Mol. Biol., 1992, pp. 319-334, vol. 224.
Stockley, P.G. et al, A Simple, RNA-Mediated Allosteric Switch Controls the Pathway to Formation of a T=3 Viral Capsid, J. Mol. Diol., 2007, pp. 541-552, vol. 369.
Strauss, J.H., Jr. and Sinsheimer, R.L., Purification and Properties of Bacteriophage MS2 and of its Ribonucleic Acid, J. Mol. Biol., 1963, pp. 43-54, vol. 7.
Studier, F.W. and Moffatt, B.A., Use of Bacteriophage T7 RNA Polymerase to Direct Selective High-level Expression of Cloned Genes, J. Mol. Biol., 1986, pp. 113-130, vol. 189.
Tars, K. et al, The Crystal Structure of Bacteriophage GA and a Comparison of Bacteriophages Belonging to the Major Groups of *Escherichia coli* Leviviruses, J. Mol. Biol., 1997, pp. 759-773, vol. 271.
The Protein Data Bank, A computer-based Archival File for Macromolecular Structures, J. Mol. Biol., 1977, pp. 535-542, vol. 112.
Toropova, K., et al, The Three-dimensional Structure of Genomic RNA in Bacteriophage MS2: Implications for Assembly, J. Mol. Biol., 2008, pp. 824-836, vol. 375.
Valegard, K. et al, The three-dimensional structure of the bacterial virus MS2, Nature, 1990, pp. 36-41, vol. 345.
Van Loo, B. et la, Directed Evolution of Epoxide Hydrolase from A. radiobacter toward Higher Enantioselectivity by Error-Prone PCR and DNA Shuffling, Chemistry and Biology, 2004, pp. 981-990, vol. 11.
Varadwaj, P.K., Lahiri, T. and Tsodikov, O., Surface Roughness Index, a novel approach to compare protein surfaces, Proceeding of International Conference on Intelligent Sensing and Information Processing, 2005, pp. 474-478.
Vogels, G., Combination of enzymatic and/or thermal pretreatment with mechanical cell disintegration, Chemical Engineering Science, 1992, pp. 123-131, vol. 47, No. 1.
Walker, S.C. and Toth, T.E., Proteolytic inactivation of simian-11 rotavirus: a pilot study, Veterinary Microbiology, 2000, pp. 195-206, vol. 74.
Wu, M. et al, Delivery of antisense oligonucleotides to leukemia cells by RNA bacteriophage capsids, Nanomedicine: Nanotechnology, Biology and Medicine, 2005, pp. 67-76, vol. 1.
Xie, J. and Schultz, P.G., A chemical toolkit for proteins- an expanded genetic code, Nature Review-Molecular Cell Biology, 2006, pp. 775-782, vol. 7.
Young, T.S. et al, An Enhanced System for Unnatural Amino Acid Mutagenesis in *E. coli*, J. Mol. Biol., 2010, pp. 361-374, vol. 395.
Strauss, James, H., et al., "Purification and Properties of Bacteriophage of MS2 and of its Ribonucleic Acid," J. Mol. Biol., vol. 7, pp. 43-54 (1963).
International Search Report of PCT/US2014/041111 dated Nov. 10, 2014.
Castanotto, D., et al., "Functional siRNA Expression from Transfected PCR Products," RNA, vol. 8, pp. 1454-1460 (Nov. 1, 2002).

(56) References Cited

OTHER PUBLICATIONS

Sasaki, J., et al., "Translation Initiation at the CUU Codon Is Mediated by the Internal Ribosome Entry Site of an Insect Picorna-Like Virus in Vitro," Journal of Virology, vol. 73, No. 2, pp. 1219-1226 (Feb. 1999).

International Search Report of PCT/US14/55426 dated Mar. 3, 2015.

Kozak, M., et al., "Fate of Maturation Protein During Infection by Coliphage MS2," Nature New Biology, vol. 234, pp. 209-211 (Dec. 15, 1971).

Kuzmanovic, D., et al., "The MS2 Coat Protein Shell is Likely Assembled Under Tension: A Novel Role for the MS2 Bacteriophage a Protein as Revealed by Small-angle Neutron Scattering," J. Mo.. Biol., vol. 355, No. 5, pp. 1095-1111 (Feb. 3, 2006).

Stockley, P., et al., "Packaging Signals in Single-Stranded RNA Viruses: Nature's Alternative to a Purely Electrostatic Assembly Mechanism," J Biol. Phys., vol. 39, pp. 277-287 (Mar. 2013).

Written Opinion of PCT/US14/55426 dated Mar. 3, 2015.

\* cited by examiner

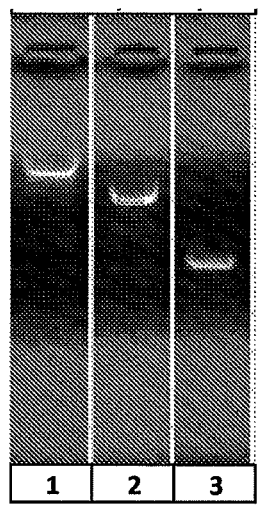 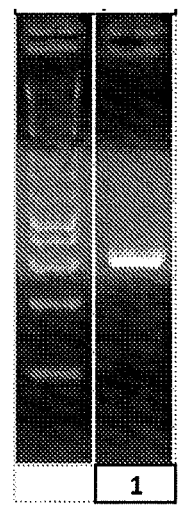
FIGURE 9        FIGURE 10

SEQUENCE LISTING

```
<160> NUMBER OF SEQ ID NOS: 6

<210> SEQ ID NO 1
<211> LENGTH: 3569
<212> TYPE: RNA
<213> ORGANISM: Bacteriophage MS2

<400> SEQUENCE: 1 ggguggggacc ccuuucgggg uccugcucaa cuuccugucg agcuaaugcc auuuuuaaug    60
ucuuuagcga dacgcuacca uggcuaucgc uguaggaugc cggaauucca uuccuaggag   120
guuugaccug ugcgagcuuu uaguacccuu gauagggaga acgagaccuu cguccccucc   180
```

| | |
|---|---|
| guucgcguuu acgcggacgg ugagacugaa gauaacucau ucucuuuaaa auaucguucg | 240 |
| aacuggacuc ccggucguuu uaacucgacu ggggccaaaa cgaaacagug gcacuacccc | 300 |
| ucuccguauu cacgggggc guuaagliguc acaucgauag aucaaggugc cuacaagcga | 360 |
| aguggguicau cgugggucg cccguacgag gagaaagccg guucggcuu cccclcgac | 420 |
| gcacgcuccu gcuacagccu cuucccugua agccaaaacu ugacuuacau cgaagugccg | 480 |
| cagaacguug cgaaccgggc gucgaccgaa guccugcaaa aggucaccca ggguaauuuu | 540 |
| aaccuuggug uugcuuuagc agaggccagg ucgacagccu cacaacucgc gacgcaaacc | 600 |
| auugcgcucg ugaaggcgua cacugccgcu cgucgcggua auuggcgcca ggcgcuccgc | 660 |
| uaccuugccc uaaacgaaga ucgaaaguuu cgaucaaaac acguggccgg caggugguug | 720 |
| gaguugcagu ucgguugguu accacuaaug agugauaucc agggugcaua ugagaugcuu | 780 |
| acgaagguuc accuucaaga guucuucccu augagagccg uacgucaggu cgguacuaac | 840 |
| aucaaguuag auggccgucu gucguauccu gcugcaaacu uccagacaac gucaacaua | 900 |
| ucgcgacgua ucgugauaug guuuuacaua aacgaugcac guuggcaug guugucgucu | 960 |
| cuagguaucu ugaacccacu agguauagug ugggaaaagg ugccuuucuc auucguugc | 1020 |
| gacuggcucc uaccguagg uaacaugcuc gagggccuua cggcccccgu gggaugcucc | 1080 |
| uacaugucag gaacaguuac ugacguaaua acgggugagu ccaucauaag cguugacgcu | 1140 |
| cccuacgggu ggacugugga gagacagggc acugcuaagg cccaaaucuc agccaugcau | 1200 |
| cgagggguac aauccguaug gccaacaacu ggcgcguacg uaaagucucc uuucucgaug | 1260 |
| guccauaccu uagaugcguu agcauuaauc aggcaacggc ucucuagaua gagcccucaa | 1320 |
| ccggaguuug aagcauggcu ucuaacuuua cucaguucgu ucucgucgac aauggcggaa | 1380 |
| cuggcgacgu gacugucgcc ccaagcaacu ucgcuaacgg ggucgcugaa uggaucagcu | 1440 |
| cuaacucgcg uucacaggcu acaaaguaa ccuguagcgu ugucagagc ucugcgcaga | 1500 |
| aucgcaaaua caccaucaaa gucgaggugc cuaaaguggc aacccagacu guuggugguug | 1560 |
| uagagcuucc uguagccgca uggcguucgu acuuaaauau ggaacuaacc auuccaauuu | 1620 |
| ucgcuacgaa uuccgacugc gagcuuauug uuaaggcaau gcaaggucuc cuaaaagaug | 1680 |
| gaaacccgau ucccucagca aucgcagcaa acuccggcau cuacuaauag acgccggcca | 1740 |
| uucaaacaug aggauuaccc augucgaaga caacaaagaa guucaacucu uauguauug | 1800 |
| aucuuccucg cgaucuuucu cucgaaauuu accaaucaau ugcuucuguc gcuacuggaa | 1860 |
| gcggugaucc gcacagugac gacuuuacag caauugcuua cuuaagggac gaauugcuca | 1920 |
| caaagcaucc gaccuuaggu ucugguaaug acgaggcgac ccgucguacc uuagcuaucg | 1980 |
| cuaagcuacg ggaggcgaau ggugaucgcg gucagauaaa uagagaaggu uucuuacaug | 2040 |
| acaaauccuu gucaugggau ccggauguuu uacaaaccag caucccguagc cuuauuggca | 2100 |
| accuccucuc uggcuaccga ucgcguugu uugggcaaug cacguucccc aacggugcuc | 2160 |
| cuaugggca caaguugcag gaugcagcgc cuuacaagaa guucgcugaa caagcaaccg | 2220 |
| uuaccccccg cgcucugaga gcggcucuau uggcucgaga ccaaugugcg ccguggauca | 2280 |
| gacacgcggu ccgcuauaac gagucauaug aauuuaggcu cguuuagggg aacgagugu | 2340 |
| uuacaguucc gaagaauaau aaaauagauc gggcugccug uaaggagccu gauaugaaua | 2400 |
| uguaccucca gaaagggguc ggugcuuuca ucagacgccg gcucaaaucc guugguauag | 2460 |
| accugaauga ucaaucgauc aaccagcguc uggcucagca gggcagcgua gauggulcgc | 2520 |
| uugcgacgau agacuuaucg ucugcauccg auuccaucuc cgaucgccug guguggaguu | 2580 |

```
uucucccacc agagcuauau ucauaucucg aucguauccg cucacacuac ggaaucguag   2640
auggcgagac gauacgaugg gaacuauuuu ccacaauggg aaaugggu uc acauuugagc   2700 uagaguccau gauauucugg gcaauaguca aagcgaccca aauccauuuu gguaacgccg   2760
gaaccauagg caucuacggg gacgauauua uaugucccag ugagauugca ccccgugugc   2820
uagaggcacu ugccuacuac gguuuuaaac cgaaucuucg uaaaacguuc guuccgggc    2880 ucuuucgcga gagcugcggc gcgcacuuuu accgugugu cgaugucaaa ccguuuuaca    2940
ucaagaaacc uguugacaau cucuucgccc ugaugcugau auuaaaucgg cuacggggu u   3000 ggggaguugu cggagguaug ucagaucc ac gccucuauaa ggugugggua cggcucuccu   3060
cccaggugcc uucgauguuc uucgguggga cggaccucgc ugccgacuac uacguaguca   3120
gcccgccuac ggcagucucg guauacacca agacuccgua cgggcggcug cucgcggaua   3180
cccguaccuc ggguuuccgu cuugcucgua ucgcucgaga acgcaaguuc uucagcgaaa   3240
agcacgacag uggucgcuac auagcguggu uccauacugg aggugaaauc accgacagca   3300
ugaaguccgc cggcgugcgc guuuauacgca cuucggagug gcuaacgccg guucccacau   3360
ucccucagga guguggccca gcagcucucuc cucgguagcu gaccgaggga ccccguaaa    3420 cggggugggu gugcucgaaa gagcacgggu gcgaaagcgg uccggcucca ccgaaaggug   3480
ggcgggcuuc ggcccaggga ccucccccua aagagaggac ccgggauucu cccgauuugg   3540
uaacuagcug cuuggcuagu uaccaccca                                    3569

<210> SEQ ID NO 2
<211> LENGTH: 393
<212> TYPE: DNA
<213> ORGANISM: Bacteriophage MS2

<400> SEQUENCE: 2
atggcttcta actttactca gttcgttctc gtcgacaatg gcggaactgg cgacgtgact     60
gtcgccccaa gcaacttcgc taacggggtc gctgaatgga tcagctctaa ctcgcgttca   120
caggcttaca agtaacctg tagcgttcgt cagagctctg cgcagaatcg caaatacacc    180
atcaaagtcg aggtgcctaa agtggcaacc cagactgttg gtggtgtaga gcttcctgta   240
gccgcatggc gttcgtactt aaatatggaa ctaaccattc aattttcgc tacgaattcc    300 gactgcgagc ttattgttaa ggcaatgcaa ggtctcctaa agatggaaa cccgattccc     360 tcagcaatcg cagcaaactc cggcatctac taa                                 393

<210> SEQ ID NO 3
<211> LENGTH: 130
<212> TYPE: PRT
<213> ORGANISM: Bacteriophage MS2

<400> SEQUENCE: 3

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Gln Asn Arg Lys Tyr Thr Ile Lys Val Glu
        50                  55                  60

Val Pro Lys Val Ala Thr Gln Thr Val Gly Gly Val Glu Leu Pro Val
65                  70                  75                  80
```

```
Ala Ala Trp Arg Ser Tyr Leu Asn Met Glu Leu Thr Ile Pro Ile Phe
            85                  90                  95

Ala Thr Asn Ser Asp Cys Glu Leu Ile Val Lys Ala Met Gln Gly Leu
           100                 105                 110

Leu Lys Asp Gly Asn Pro Ile Pro Ser Ala Ile Ala Ala Asn Ser Gly
       115                 120                 125

Ile Tyr
    130

<210> SEQ ID NO 4
<211> LENGTH: 480
<212> TYPE: DNA
<213> ORGANISM: Artificial Sequence
<220> FEATURE:
<223> OTHER INFORMATION: Bacteriophage MS2 capsid protein and pac
      sequence cloning cassette
<220> FEATURE:
<221> NAME/KEY: gene
<222> LOCATION: (42)..(435)
<220> FEATURE:
<221> NAME/KEY: stem_loop
<222> LOCATION: (454)..(472)
<223> OTHER INFORMATION: pac sequence

<400> SEQUENCE: 4
acaagtttgt acaaaaaagc aggctaagaa ggagatatac atatggcttc taactttact    60
cagttcgttc tcgtcgacaa tggcggaact ggcgacgtga ctgtcgcccc aagcaacttc   120
gctaacgggg tcgctgaatg gatcagctct aactcgcgtt cacaggctta caaagtaacc   180
tgtagcgttc gtcagagctc tgcgcagaat cgcaaataca ccatcaaagt cgaggtgcct   240
aaagtggcaa cccagactgt tggtggtgta gagcttcctg tagccgcatg gcgttcgtac   300
ttaaatatgg aactaaccat tccaattttc gctacgaatt ccgactgcga gcttattgtt   360
aaggcaatgc aaggtctcct aaaagatgga aacccgattc cctcagcaat cgcagcaaac   420
tccggcatct actaatagac gccggccatt caaacatgag gattacccat gtacccagct   480

<210> SEQ ID NO 5
<211> LENGTH: 435
<212> TYPE: DNA
<213> ORGANISM: Artificial Sequence
<220> FEATURE:
<223> OTHER INFORMATION: Bacteriophage MS2 capsid protein cloning
      cassette
<220> FEATURE:
<221> NAME/KEY: gene
<222> LOCATION: (42)..(435)
<223> OTHER INFORMATION: Bacteriophage MS2 coat protein

<400> SEQUENCE: 5
acaagtttgt acaaaaaagc aggctaagaa ggagatatac atatggcttc taactttact    60
cagttcgttc tcgtcgacaa tggcggaact ggcgacgtga ctgtcgcccc aagcaacttc   120
gctaacgggg tcgctgaatg gatcagctct aactcgcgtt cacaggctta caaagtaacc   180
tgtagcgttc gtcagagctc tgcgcagaat cgcaaataca ccatcaaagt cgaggtgcct   240
aaagtggcaa cccagactgt tggtggtgta gagcttcctg tagccgcatg gcgttcgtac   300
ttaaatatgg aactaaccat tccaattttc gctacgaatt ccgactgcga gcttattgtt   360
aaggcaatgc aaggtctcct aaaagatgga aacccgattc cctcagcaat cgcagcaaac   420
tccggcatct actaa                                                    435
```

```
<210> SEQ ID NO 6
<211> LENGTH: 251
<212> TYPE: DNA
<213> ORGANISM: Artificial Sequence
<220> FEATURE:
<223> OTHER INFORMATION: Heterologous cargo molecule
<220> FEATURE:
<221> NAME/KEY: promoter
<222> LOCATION: (1)..(18)
<223> OTHER INFORMATION: T7
<220> FEATURE:
<221> NAME/KEY: misc_RNA
<222> LOCATION: (19)..(98)
<223> OTHER INFORMATION: ribozyme
<220> FEATURE:
<221> NAME/KEY: stem_loop
<222> LOCATION: (99)..(145)
<223> OTHER INFORMATION: shRNA
<220> FEATURE:
<221> NAME/KEY: misc_RNA
<222> LOCATION: (146)..(226)
<223> OTHER INFORMATION: ribozyme
<220> FEATURE:
<221> NAME/KEY: stem_loop
<222> LOCATION: (227)..(246)
<223> OTHER INFORMATION: pac sequence

<400> SEQUENCE: 6
taatacgact cactataggg agaacgccgg ccattcaaat agtaaataat agagggtcag     60
cttgctgatg aggcgcttcg gcgccgaaac accgtgtcca agctgaccct gaagttcatc    120
aagagtgaac ttcagggtca gcttgtcacc ggatgtgctc tccggtctga tgagtccgtg    180
aggacgaaac aagctgaccc tgaagttcac tacgccggcc attcaaacat gaggattacc    240
catgtccatg g                                                         251
```

PROCESS FOR PURIFYING VLPS

CROSS REFERENCE TO RELATED APPLICATIONS

This application is a continuation of U.S. application Ser. No. 13/725,184, filed Dec. 21, 2012, which claims the priority of U.S. Provisional Application No. 61/578,706 filed Dec. 21, 2011, U.S. Provisional Application No. 61/607,900 filed Mar. 7, 2012, and U.S. Provisional Application No. 61/661,688 filed Jun. 19, 2012, the entire disclosures of which are hereby incorporated by reference.

INCORPORATION OF SEQUENCE LISTING

The entire contents of a paper copy of the "Sequence Listing" and a computer readable form of the sequence listing on optical disk, containing a file named FINAL_APSE_SEQ_ST25.txt, which is 10 kilobytes in size and was created on May 15, 2014, are herein incorporated by reference.

TECHNICAL FIELD

The invention relates to virus-like particles, and in particular to processes for producing, isolating and purifying virus-like particles containing heterologous cargo molecules.

BACKGROUND OF THE INVENTION

Virus-like particles (VLPs) are particles derived in part from viruses through the expression of certain viral structural proteins which make up the viral envelope and/or capsid, but VLPs do not contain the viral genome and are non-infectious. VLPs have been derived for example from the Hepatitis B virus and certain other viruses, and have been used to study viral assembly and in vaccine development.

Viral capsids are composed of at least one protein, several copies of which assemble to form the capsid. In some viruses, the viral capsid is covered by the viral envelope. Such viral envelopes are comprised of viral glycoproteins and portions of the infected host's cell membranes, and shield the viral capsids from large molecules that would otherwise interact with them. The capsid is typically said to encapsidate the nucleic acids which encode the viral genome and sometimes also proteins necessary for the virus' persistence in the natural environment. For the viral genome of a virus to enter a new host, the capsid must be disassembled. Such disassembly happens under conditions normally used by the host to degrade its own as well as foreign components, and most often involves proteolysis. Viruses take advantage of normal host processes such as proteolytic degradation to enable that critical part of their cycle, i.e. capsid disassembly and genome release.

It is therefore unsurprising that the literature has not previously described capsids resistant to hydrolases that act on peptide bonds. A very limited number of certain specific peptide sequences which are part of larger proteins are known to be somewhat resistant to certain proteases, but the vast majority of peptide sequences are not. Viruses that resist proteolysis have been reported, but these are all enveloped viruses, in which the capsid is shielded by the viral envelope. In such viruses the capsids are not in contact with, i.e. they are shielded from the proteases described. Thus the role, if any, of the proteolytical stability of the virus capsid in such cases is unknown.

In large-scale manufacturing of recombinant molecules such as proteins, ultrafiltration is often used to remove molecules smaller than the target protein in the purification steps leading to its isolation. Purification methods also often involve precipitation, solvent extraction, and crystallization techniques. These separation techniques are inherently simple and low cost because, in contrast to chromatography, they are not based on surface but on bulk interactions. However, these techniques are typically limited to applications to simple systems, and by the need to specify a different set of conditions for each protein and expression system. Yet each target recombinant protein presents a unique set of interactions, thereby making its isolation process unique and complex. The separation efficiency for recombinant proteins using these simple isolation processes is therefore low.

Nucleic acids, including siRNA and miRNA, have for the most part been manufactured using chemical synthesis methods. These methods are generally complex and high cost because of the large number of steps needed and the complexity of the reactions which predispose technical difficulties, and the cost of the manufacturing systems. In addition, the synthetic reagents involved are costly and so economy of scale is not easily obtained by simply increasing batch size. In large-scale manufacturing of recombinant molecules such as proteins, ultrafiltration is often used to remove molecules smaller than the target protein in the purification steps leading to its isolation. Purification methods also often involve precipitation, solvent extraction, and crystallization techniques. These separation techniques are inherently simple and low cost because, in contrast to chromatography, they are not based on surface but on bulk interactions. However, these techniques are typically limited to applications to simple systems, and by the need to specify a different set of conditions for each protein and expression system. Yet each target recombinant protein presents a unique set of interactions, thereby making its isolation process unique and complex. The separation efficiency for recombinant proteins using these simple isolation processes is therefore low.

BRIEF SUMMARY OF THE INVENTION

In one aspect the present disclosure provides a method for producing a virus-like particle (VLP) comprising a capsid enclosing at least one heterologous cargo molecule.

VLPs according to the present disclosure may comprise a capsid which comprises a wild type viral capsid which is resistant to hydrolysis catalyzed by a peptide bond hydrolase category E.C. 3.4, or a capsid protein having at least 15%, at least 16%, at least 21%, at least 40%, at least 41%, at least 45%, at least 52%, at least 53%, at least 56%, at least 59% or at least 86% sequence identity with the amino acid sequence of wild type Enterobacteria phage MS2 capsid protein (SEQ ID NO: 3). The capsid may comprise a wild type Enterobacteria phage MS2 capsid protein having the amino acid sequence of SEQ ID NO: 3.

VLPs according to the present disclosure may comprise a heterologous cargo molecule comprising a peptide or polypeptide. A VLP may further comprise an oligonucleotide linker coupling the heterologous cargo peptide or polypeptide molecule and the viral capsid.

In another aspect, the present disclosure provides a nucleic acid construct comprising a nucleotide sequence that encodes an RNA. The RNA may be for example an siRNA or an shRNA. The present disclosure also encompasses a vector comprising any such nucleic acid constructs, and host cells comprising such a vector, as well as host cell stably transformed with such a vector. Host cells may be a bacterial cell, such as but not limited to an *Escherichia coli* cell, a plant cell, a mammalian cell, an insect cell, a fungal cell or a yeast cell. A host cell may further be stably transfected with a second vector comprising a second nucleic acid sequence encoding a viral capsid. The second nucleic acid sequence may encode for example a viral protein encoding a viral capsid having at least 40% sequence identity with the amino acid sequence of wild type Enterobacteria phage MS2 capsid protein (SEQ ID NO: 3). A nucleic acid construct as described herein may also encode a wild type Enterobacteria phage MS2 capsid protein (SEQ ID NO: 3). The present disclosure also encompasses a plant or plant tissue transformed to contain a nucleic acid construct described herein, and seed or progeny of such a plant or plant tissue, wherein the seed or progeny comprises the nucleic acid construct.

In another aspect, the present disclosure provides a composition comprising: a) a plurality of virus-like particles each comprising a viral capsid enclosing at least one heterologous cargo molecule; and b) one or more cell lysis products present in an amount of less than 4 grams for every 100 grams of capsid present in the composition, wherein the cell lysis products are selected from proteins, polypeptides, peptides and any combination thereof. In the composition, the capsid is for example resistant to hydrolysis catalyzed by a peptide bond hydrolase category E.C. 3.4. Such VLPs in a composition may further comprise an oligonucleotide linker coupling the heterologous cargo molecule and the viral capsid.

In another aspect, the present disclosure provides method for isolating and purifying a target cargo molecule, the method comprising: (a) obtaining a whole cell lysate comprising a plurality of virus-like particles (VLPs) each comprising a capsid enclosing at least one target cargo molecule, wherein the capsids are resistant to hydrolysis catalyzed by a peptide bond hydrolase category E.C. 3.4; (b) subjecting the VLP's to hydrolysis using a peptide bond hydrolase category E.C. 3.4, for a time and under conditions sufficient for at least 60, at least 70, at least 80, or at least 90 of every 100 individual polypeptides present in the whole cell lysate but not enclosed by the capsids to be cleaved, while at least 60, at least 70, at least 80, or at least 90 of every 100 capsids present in the whole cell lysate before such hydrolysis remain intact following the hydrolysis. In the method, the capsids may each comprise a viral capsid protein having at least 15%, at least 16%, at least 21%, at least 40%, at least 41%, at least 45%, at least 52%, at least 53%, at least 56%, at least 59% or at least 86% sequence identity with the amino acid sequence of wild type Enterobacteria phage MS2 capsid protein (SEQ ID NO: 3). The capsids may each comprise a wild type Enterobacteria phage MS2 capsid protein (SEQ ID NO: 3). In the method, the heterologous cargo molecule may comprise an oligonucleotide which may be an oligoribonucleotide, or a peptide or a polypeptide. An oligoribonucleotide may be selected for example from siRNA, shRNA, sshRNA, lshRNA and miRNA. The method may further comprise purification of the capsids following hydrolysis. Purification may include at least one of a liquid-liquid extraction step, a crystallization step, a fractional precipitation step, and an ultra filtration step. The present disclosure also encompasses a composition produced by such a method.

In another aspect, the present disclosure provides a method for protecting a target molecule from hydrolysis in a whole cell lysate following intracellular production of the target molecule in a host cell, the method comprising: (a) selecting a viral capsid which is resistant to hydrolysis catalyzed by a peptide bond hydrolase category E.C. 3.4; (b) stably transfecting the host cell with a first vector comprising a nucleic acid sequence encoding a viral protein forming the viral capsid, and a second vector comprising a nucleic acid sequence comprising a sequence encoding a cargo molecule; and (c) maintaining the cells for a time and under conditions sufficient for the transformed cells to express capsid protein and assemble capsids encapsidating the cargo molecule. In the process, the capsids may each comprise a viral capsid protein having at least 15%, at least 16%, at least 21%, at least 40%, at least 41%, at least 45%, at least 52%, at least 53%, at least 56%, at least 59% or at least 86% sequence identity with the amino acid sequence of wild type Enterobacteria phage MS2 capsid protein (SEQ ID NO: 3).

In another aspect, the present disclosure provides a process for purifying VLPs enclosing at least one heterologous cargo molecule, the process comprising: (a) obtaining a cell lysate comprising a plurality of the VLPs; (b) contacting the cell lysate with a protease for a time and under conditions sufficient to hydrolyze cell lysis products other than the VLPs to form a hydrolysate; and (c) isolating the VLPs from the hydrolsyate. Step (c) may comprise (i) performing a first precipitation with ammonium sulfate followed by a first centrifugation to obtain a first precipitate and a first supernatant; and (ii) performing a second precipitation on the first supernatant with ammonium sulfate followed by a second centrifugation to obtain a second precipitate, wherein the second precipitate comprises at least about 70%, 80% or 90% by weight of the VLPs. Step (c) may comprise (i) performing a first precipitation with ethanol followed by a first centrifugation to obtain a first precipitate and a first supernatant; and (ii) performing a second precipitation on the first supernatant with ammonium sulfate followed by a second centrifugation to obtain a second precipitate, wherein the second precipitate comprises at least about 70%, 80% or 90% by weight of the VLPs. Step (c) may comprise ultracentrifuging the hydrolysate to obtain a precipitate comprising at least about 70%, 80% or 90% by weight of the VLPs. In the process, the VLPs may each comprise a capsid which is resistant to hydrolysis catalyzed by a peptide bond hydrolase category E.C. 3.4, which can comprise a capsid protein having at least 15%, at least 16%, at least 21%, at least 40%, at least 41%, at least 45%, at least 52%, at least 53%, at least 56%, at least 59% or at least 86% sequence identity with the amino acid sequence of wild type Enterobacteria phage MS2 capsid protein (SEQ ID NO: 3). The VLPs may each comprise a wild type Enterobacteria phage MS2 capsid protein (SEQ ID NO: 3). In the process, step (b) can be performed for at least about 30 minutes at about 37° C. The process may further comprise, before step (b), contacting the cell lysate with at least one of a nuclease, an amylase and a lipase for at least about 30 minutes at about 37° C. In the process, the protease can be for example a peptide bond hydrolase category E.C. 3.4, which can be selected for example from Proteinase K, Protease from *Streptomyces griseus*, Protease from *Bacillus licheniformis*, pepsin and papain. In the process, the heterologous cargo molecule enclosed by the VLPs may comprise an oligonucleotide which may be an oligoribonucleotide, or a peptide or a polypeptide. An oligoribonucleotide may be selected for example from siRNA, shRNA, sshRNA, lshRNA and miRNA. The process may further comprise preparing the cell lysate before step (a) by centrifuging cells following expression of the VLPs in the cells; resuspending the cells; lysing the cells and centrifuging the cell lysate to obtain a supernatant, wherein the supernatant is used as the cell lysate for step (a).

In another aspect, the present disclosure provides VLPs comprising a capsid enclosing at least one heterologous cargo molecule and a packing sequence wherein the capsid comprises a capsid protein which is a variant of wild type Enterobacteria phage MS2 capsid protein (SEQ ID NO: 3). The capsid protein may be one which has the amino acid sequence of wild type Enterobacteria phage MS2 capsid protein (SEQ ID NO: 3) except that the A residue at position 1 is deleted. The capsid protein may be one which has the amino acid sequence of wild type Enterobacteria phage MS2 capsid protein (SEQ ID NO:3) except that the A residue at position 1 is deleted and the S residue at position 2 is deleted. The capsid protein may be one which has the amino acid sequence of wild type Enterobacteria phage MS2 capsid protein (SEQ ID NO: 3) except that the A residue at position 1 is deleted, the S residue at position 2 is deleted and the N residue at position 3 is deleted. The capsid protein may be one which has the amino acid sequence of wild type Enterobacteria phage MS2 capsid protein (SEQ ID NO: 3) except that the Y reside at position 129 is deleted. The capsid protein may be one which has the amino acid sequence of wild type Enterobacteria phage MS2 capsid protein (SEQ ID NO:3) but having a single (1) amino acid deletion in the 112-117 segment. The capsid protein may be one which has the amino acid sequence of wild type Enterobacteria phage MS2 capsid protein (SEQ ID NO:3) but having a single (1) amino acid deletion in the 112-117 segment. The capsid protein may be one which has the amino acid sequence of wild type Enterobacteria phage MS2 capsid protein (SEQ ID NO:3) but having a 1-2 residue insertion in the 65-83 segment. The capsid protein may be one which has the amino acid sequence of wild type Enterobacteria phage MS2 capsid protein (SEQ ID NO:3) but having a 1-2 residue insertion in the 44-55 segment. The capsid protein may be one which has the amino acid sequence of wild type Enterobacteria phage MS2 capsid protein (SEQ ID NO:3) but having a single (1) residue insertion in the 33-43 segment. The capsid protein may be one which has the amino acid sequence of wild type Enterobacteria phage MS2 capsid protein (SEQ ID NO:3) but having a 1-2 residue insertion in the 24-30 segment. The capsid protein may be one which has the amino acid sequence of wild type Enterobacteria phage MS2 capsid protein (SEQ ID NO:3) but having a single (1) residue insertion in the 10-18 segment. The capsid may comprise a capsid protein monomer sequence concatenated with a second capsid protein monomer sequence which assembles into a capsid which resistant to hydrolysis catalyzed by a peptide bond hydrolase category E.C. 3.4. The capsid may comprise a capsid protein monomer sequence whose C-terminus is extended with a 0-6 residue linker segment whose C-terminus is concatenated with a second capsid protein monomer sequence, all of which assembles into a capsid which is resistant to hydrolysis catalyzed by a peptide bond hydrolase category E.C. 3.4. A linker segment may have a sequence such as, for example, -(Gly)$_x$-, wherein x=0-6. A linker segment may be a Gly-Ser linker selected from -Gly-Gly-Ser-Gly-Gly-, -Gly-Gly-Ser and -Gly-Ser-Gly- The capsid may comprise the capsid protein concatenated with a third capsid protein monomer sequence which assembles into a capsid which is resistant to hydrolysis catalyzed by a peptide bond hydrolase category E.C. 3.4. The capsid may comprise a capsid protein wherein the C-terminus is extended with a 0-6 residue linker segment whose C-terminus is concatenated with a third capsid protein monomer sequence, all of which assembles into a capsid which is resistant to hydrolysis catalyzed by a peptide bond hydrolase category E.C. 3.4. The capsid may comprise a capsid protein wherein the capsid comprises a capsid protein in which one or both linker sequences is -(Gly)$_x$, wherein x=0-6, including -Gly-; -Gly-Gly-; and -Gly-Gly-Gly-. A linker segment may be a Gly-Ser linker selected from -Gly-Gly-Ser-Gly-Gly-, -Gly-Gly-Ser and -Gly-Ser-Gly-. Such a capsid protein assembles for example into a capsid which is resistant to hydrolysis catalyzed by a peptide bond hydrolase category E.C. 3.4. For example, the capsid may comprise a capsid protein in which one or both linker sequences is -(Gly)$_x$-, x=1, which assembles into a capsid which is resistant to hydrolysis catalyzed by a peptide bond hydrolase category E.C. 3.4. The capsid may comprise a capsid protein in which one or both linker sequences is -(Gly)$_x$-, x=2, which assembles into a capsid which is resistant to hydrolysis catalyzed by a peptide bond hydrolase category E.C. 3.4. The capsid may comprise a capsid protein in which one or both linker sequences is -(Gly)$_x$-, x=3, which assembles into a capsid which is resistant to hydrolysis catalyzed by a peptide bond hydrolase category E.C. 3.4. The capsid may comprise one or more capsid protein sequences which is N-terminally truncated by 1-3 residues and a linker segment as described herein is lengthened by the number of residues deleted. The capsid may comprise one or more capsid protein sequences which is C-terminally truncated by 1 residue, and linker segments as described herein are lengthened by the one residue, wherein the capsid is resistant to hydrolysis catalyzed by a peptide bond hydrolase category E.C. 3.4. The capsid may comprise a first capsid protein sequence in a concatenated dimer which is C-terminally truncated by 1 residue and the linker segments lengthened by the one residue or wherein the first and/or second capsid protein sequence in a concatenated trimer is C-terminally truncated by 1 residues. The capsid may comprise a capsid protein having N- and C-terminal truncations.

BRIEF DESCRIPTION OF THE DRAWINGS

FIG. 9 is a chromatograph of PCR products obtained from an MS2 sample following purification described for FIGS. 5 and 6, chromatographed in 1.5% agarose gel stained with Ethidium Bromide (1.2 kbp for primers F1201_1223-R1979_2001 in Lane 1, 800 bp for primers F1201_1223-R1979_2001 in Lane 2, and 304 bp for primers F1401_1426-R1680_1705 in Lane 3), showing consistency with an intact MS2 bacteriophage genome.

FIG. 10 is a chromatograph of PCR products from PCR interrogation of an VLP sample for presence or absence of a section of the MS2 capsid protein following purification, chromatographed in 2% agarose gel stained with Ethidium Bromide (304 bp in Lane 1; the leftmost Lane corresponds to 1 kb plus ladder from Life Technologies), showing consistency with an intact MS2 capsid protein gene.

Figure 11:
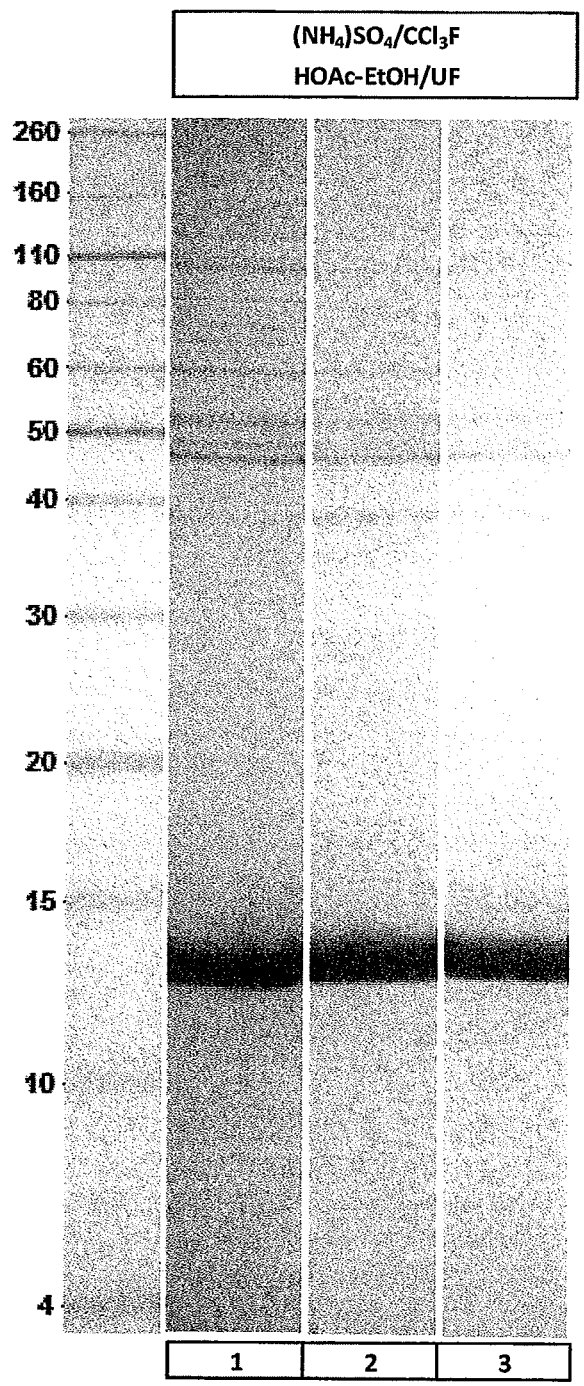

FIG. 11 is a gel showing results of SDS-PAGE analysis of VLP samples following simple precipitation with ethanol.

Figure 12:
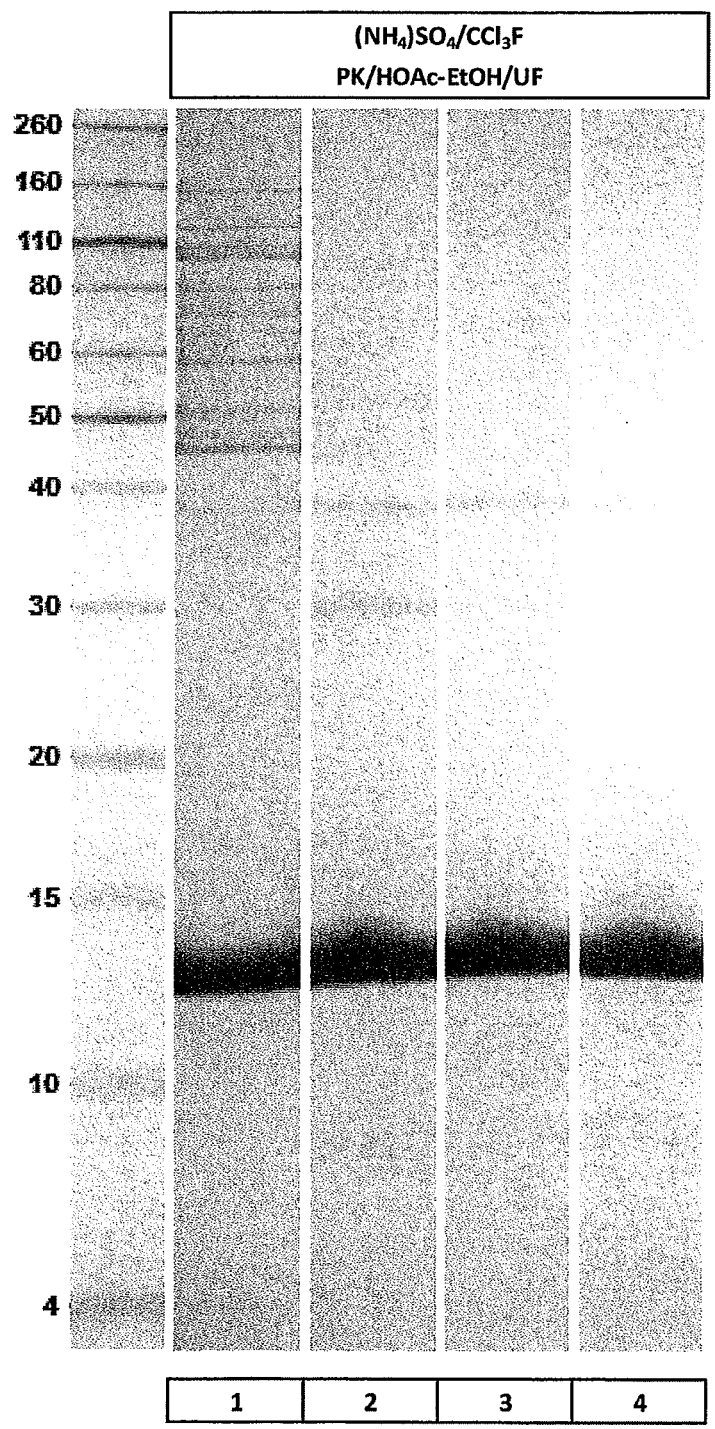

FIG. 12 is a gel showing results of SDS-PAGE analysis of VLP samples following use of Proteinase K and simple precipitation with ethanol for purification of MS2 VLPs.

Figure 13:
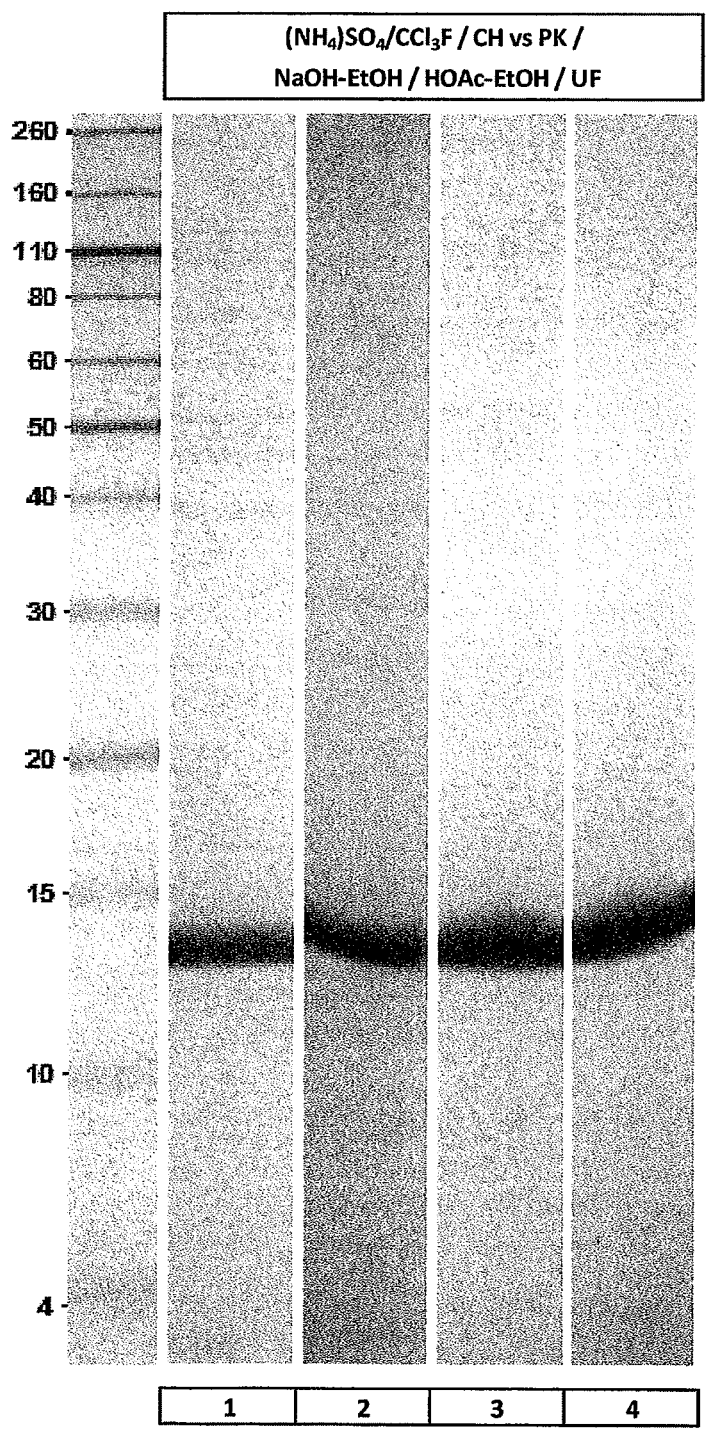

FIG. 13 is a gel showing results of SDS-PAGE analysis of MS2 samples following use of constitutive hydrolases, fractional precipitation with ethanol, and ultrafiltration for purification of VLPs.

Figure 14:
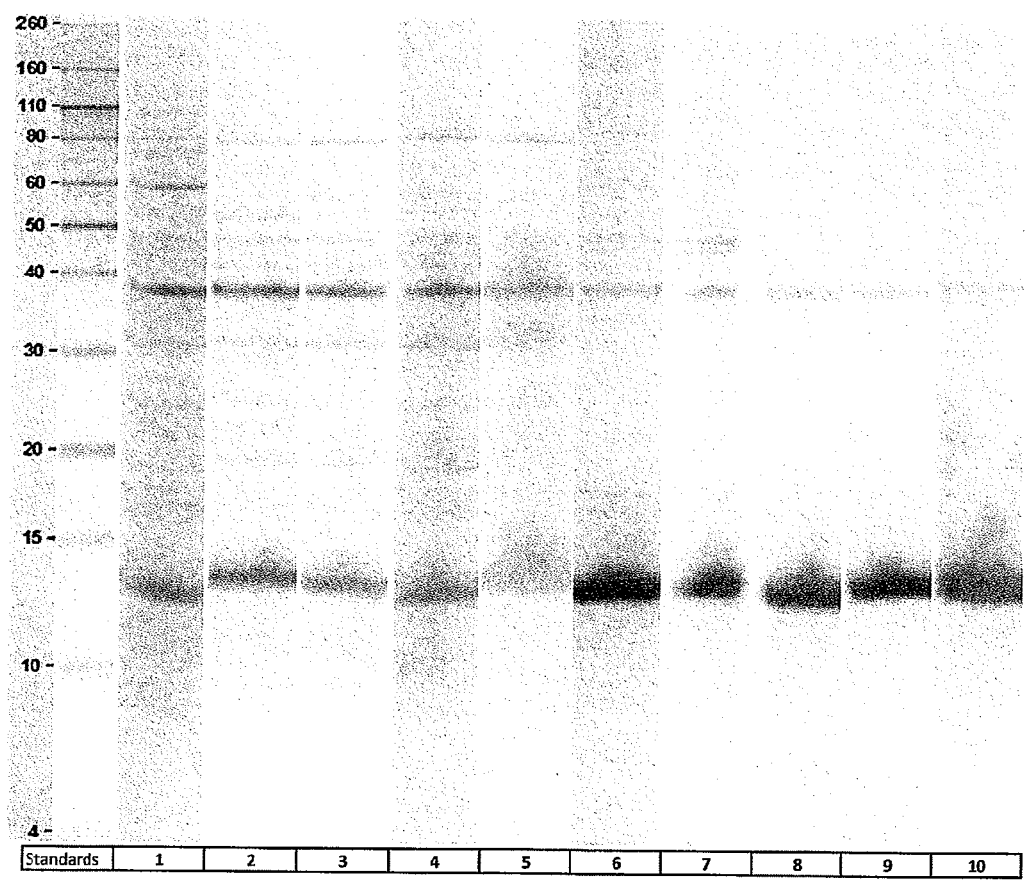

FIG. 14 is a gel showing results of SDS-PAGE analysis of VLP samples following use of various hydrolases, and fractional precipitation with ammonium sulfate for purification of VLPs.

Figure 15:
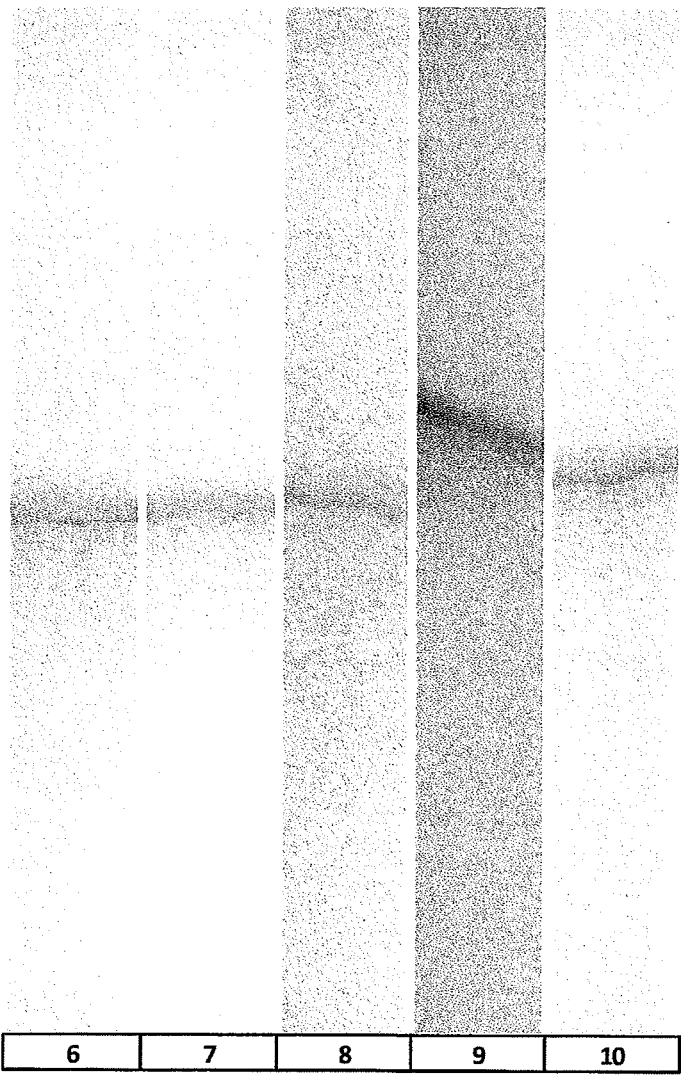

FIG. 15 is a gel showing results of PAGE analysis of RNA obtained from RNA encapsidated in VLPs.

Figure 16:
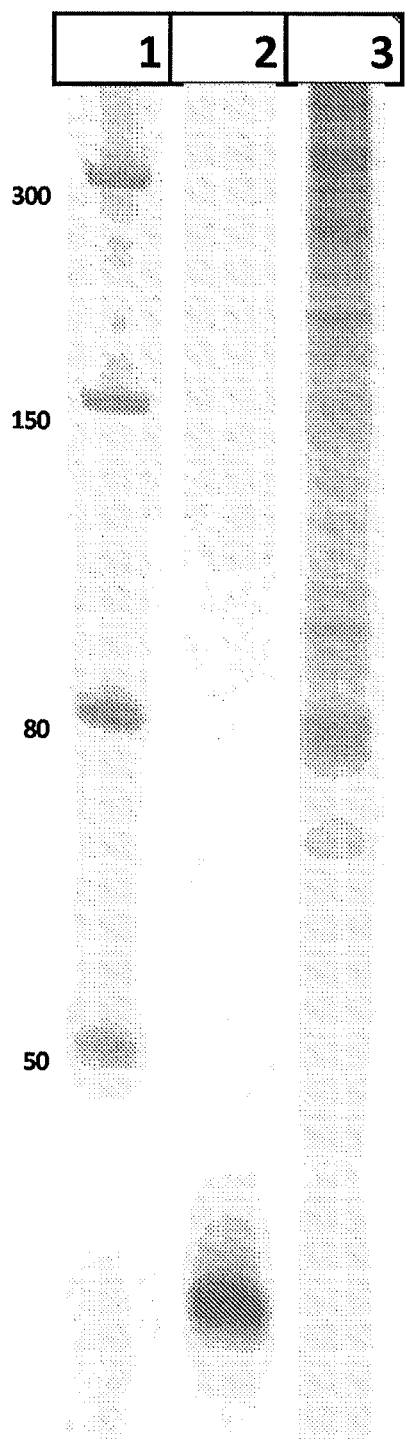

FIG. 16 is a gel showing results of PAGE analysis of RNA products obtained from RNA encapsidated in VLPs, following purification of the VLP's and isolation of the RNA from the VLPs.

Figure 17:
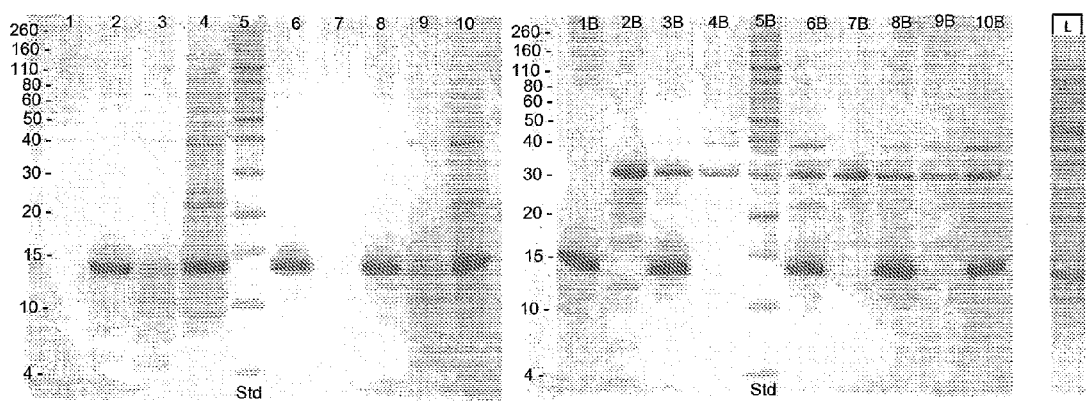

FIG. 17 is a series of gels showing results of SDS-PAGE analyses of VLP's comprising MS2 capsids, following purification and suspension of the VLPs, and exposure to various proteases for 1 hour and 4 hours of incubation.

DETAILED DESCRIPTION OF THE INVENTION

Section headings as used in this section and the entire disclosure herein are not intended to be limiting.

A. Definitions

A wide variety of conventional techniques and tools in chemistry, biochemistry, molecular biology, and immunology are employed and available for practicing the methods and compositions described herein, are within the capabilities of a person of ordinary skill in the art and well described in the literature. Such techniques and tools include those for generating and purifying VLPs including those with a wild type or a recombinant capsid together with the cargo molecule(s), and for transforming host organisms and expressing recombinant proteins and nucleic acids as described herein. See, e.g., MOLECULAR CLONING, A LABORATORY MANUAL 2nd ed. 1989 (Sambrook et al, Cold Spring Harbor Laboratory Press); and CURRENT PROTOCOLS IN MOLECULAR BIOLOGY (Eds. Ausubel et al, Greene Publ. Assoc., Wiley-Interscience, NY) 1995. The disclosures in each of these are herein incorporated by reference.

As used herein, the term "cargo molecule" refers to an oligonucleotide, polypeptide or peptide molecule, which is or may be enclosed by a capsid.

As used herein, the term "oligonucleotide" refers to a short polymer of at least two, and no more than about 70 nucleotides, preferably no more than about 55 nucleotides linked by phosphodiester bonds. An oligonucleotide may be an oligodeoxyribonucleotide (DNA) or a oligoribonucleotide (RNA), and encompasses short RNA molecules such as but not limited to siRNA, shRNA, sshRNA, lshRNA, and miRNA.

As used herein, the term "peptide" refers to a polymeric molecule which minimally includes at least two amino acid monomers linked by peptide bond, and preferably has at least about 10, and more preferably at least about 20 amino acid monomers, and no more than about 60 amino acid monomers, preferably no more than about 50 amino acid monomers linked by peptide bonds. For example, the term encompasses polymers having about 10, about 20, about 30, about 40, about 50, or about 60 amino acid residues.

As used herein, the term "polypeptide" refers to a polymeric molecule including at least one chain of amino acid monomers linked by peptide bonds, wherein the chain includes at least about 70 amino acid residues, preferably at least about 80, more preferably at least about 90, and still more preferably at least about 100 amino acid residues. As used herein the term encompasses proteins, which may include one or more linked polypeptide chains, which may or may not be further bound to cofactors or other proteins. The term "protein" as used herein is used interchangeably with the term "polypeptide."

As used herein, the term "variant" with reference to a molecule is a sequence that is substantially similar to the sequence of a native or wild type molecule. With respect to nucleotide sequences, variants include those sequences that may vary as to one or more bases, but because of the degeneracy of the genetic code, still encode the identical amino acid sequence of the native protein. Variants include naturally occurring alleles, and nucleotide sequences which are engineered using well-known techniques in molecular biology, such as for example site-directed mutagenesis, and which encode the native protein, as well as those that encode a polypeptide having amino acid substitutions. Generally, nucleotide sequence variants of the invention have at least 40%, at least 50%, at least 60%, at least 70% or at least 80% sequence identity to the native (endogenous) nucleotide sequence. The present disclosure also encompasses nucleotide sequence variants having at least about 85% sequence identity, at least about 90% sequence identity, at least about 85%, 86%, 87%, 88%, 89%, 90% 91%, 92%, 93%, 94%, 95%, 96%, 97%, 98%, 99%.

Sequence identity of amino acid sequences or nucleotide sequences, within defined regions of the molecule or across the full-length sequence, can be readily determined using conventional tools and methods known in the art and as described herein. For example, the degree of sequence identity of two amino acid sequences, or two nucleotide sequences, is readily determined using alignment tools such as the NCBI Basic Local Alignment Search Tool (BLAST) (Altschul et al., 1990), which are readily available from multiple online sources. Algorithms for optimal sequence alignment are well known and described in the art, including for example in Smith and Waterman, Adv. Appl. Math. 2:482 (1981); Pearson and Lipman Proc. Natl. Acad. Sci. (U.S.A.) 85: 2444 (1988). Algorithms for sequence analysis are also readily available in programs such as blastp, blastn, blastx, tblastn and tblastx. For the purposes of the present disclosure, two nucleotide sequences may be also considered "substantially identical" when they hybridize to each other under stringent conditions. Stringent conditions include high hybridization temperatures and low salt hybridization buffers which permit hybridization only between nucleic acid sequences that are highly similar. Stringent conditions are sequence-dependent and will be different in different circumstance, but typically include a temperature at least about 60°

C., which is about 10° C. to about 15° C. lower than the thermal melting point (Tm) for the specific sequence at a defined ionic strength and pH. Salt concentration is typically about 0.02 molar at pH 7.

As used herein with respect to a given nucleotide sequence, the term "conservative variant" refers to a nucleotide sequence that encodes an identical or essentially identical amino acid sequence as that of a reference sequence. Due to the degeneracy of the genetic code, whereby almost always more than one codon may code for each amino acid, nucleotide sequences encoding very closely related proteins may not share a high level of sequence identity. Moreover, different organisms have preferred codons for many amino acids, and different organisms or even different strains of the same organism, e.g., E coli strains, can have different preferred codons for the same amino acid. Thus, a first nucleotide acid sequence which encodes essentially the same polypeptide as a second nucleotide acid sequence is considered substantially identical to the second nucleotide sequence, even if they do not share a minimum percentage sequence identity, or would not hybridize to one another under stringent conditions. Additionally, it should be understood that with the limited exception of ATG, which is usually the sole codon for methionine, any sequence can be modified to yield a functionally identical molecule by standard techniques, and such modifications are encompassed by the present disclosure. As described herein below, the present disclosure specifically contemplates protein variants of a native protein, which have amino acid sequences having at least 15%, at least 16%, at least 21%, at least 40%, at least 41%, at least 52%, at least 53%, at least 56%, at least 59% or at least 86% sequence identity to a native nucleotide sequence.

The degree of sequence identity between two amino acid sequences may be determined using the BLASTp algorithm of Karlin and Altschul (Proc. Natl. Acad. Sci. USA 87:2264-2268, 1993). The percentage of sequence identity is determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which an identical amino acid occurs in both sequences to yield the number of matched positions, dividing the number of matched positions by the total number of positions in the window of comparison and multiplying the result by 100 to yield the percentage of sequence identity.

One of skill will recognize that polypeptides may be "substantially similar", in that an amino acid may be substituted with a similar amino acid residue without affecting the function of the mature protein. Polypeptide sequences which are "substantially similar" share sequences as noted above except that residue positions, which are not identical, may have conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acid substitution groups include: valine-leucine-isoleucine, phenylalanine-tyrosine, lysine-arginine, alanine-valine, and asparagine-glutamine.

A nucleic acid encoding a peptide, polypeptide or protein may be obtained by screening selected cDNA or genomic libraries using a deduced amino acid sequence for a given protein. Conventional procedures using primer extension procedures, as described for example in Sambrook et al, can be used to detect precursors and processing intermediates.

B. Virus-Like Particles (VLPs) Composed of a Capsid Enclosing a Cargo Molecule

The methods and compositions described herein are the result in part of the appreciation that certain viral capsids can be prepared and/or used in novel manufacturing and purification methods to improve commercialization procedures for nucleic acids, peptides and proteins. The methods described herein use recombinant viral capsids which are resistant to readily available hydrolases, to enclose heterologous cargo molecules such as nucleic acids, peptides, or polypeptides including proteins.

The capsid may be a wild type capsid or a mutant capsid derived from a mutant capsid protein or a wild type capsid protein, provided that the capsid exhibits resistance to hydrolysis catalyzed by at least one hydrolase acting on peptide bonds when the capsids are contacted with the hydrolase. As used interchangeably herein, the phrases "resistance to hydrolysis" and "hydrolase resistant" refer to any capsid which, when present in a whole cell lysate also containing polypeptides which are cell lysis products and not enclosed in the capsids, and subjected to hydrolysis using a peptide bond hydrolase category E.C. 3.4 for a time and under conditions sufficient for at least 60, at least 70, at least 80, or at least 90 of every 100 individual polypeptides present in the lysate (which are cell lysis products and not enclosed in the capsids) to be cleaved (i.e. at least 60%, at least 70%, at least 80%), or at least 90% of all individual unenclosed polypeptides are cleaved), yet at least 60, at least 70, at least 80, or at least 90 of every 100 capsids present before such hydrolysis remain intact following the hydrolysis. Hydrolysis may be conducted for a period of time and under conditions sufficient for the average molecular weight of cell proteins remaining from the cell line following hydrolysis is less than about two thirds, less than about one half, less than about one third, less than about one fourth, or less than about one fifth, of the average molecular weight of the cell proteins before the hydrolysis is conducted. Methods may further comprise purifying the intact capsid remaining after hydrolysis, and measuring the weight of capsids and the weight of total dry cell matter before and after hydrolysis and purification, wherein the weight of capsids divided by the weight of total dry cell matter after hydrolysis and purification is at least twice the weight of capsids divided by the weight of total dry cell matter measured before the hydrolysis and purification. The weight of capsids divided by the weight of total dry cell matter after hydrolysis and purification may be at least 10 times more than, preferably 100 times more than, more preferably 1,000 times more than, and most preferably 10,000 times more than the weight of capsids divided by the weight of total dry cell matter measured before such hydrolysis and purification.

Hydrolases are enzymes that catalyze hydrolysis reactions classified under the identity number E.C. 3 by the Enzyme Commission. For example, enzymes that catalyze hydrolysis of ester bonds have identity numbers starting with E.C. 3.1. Enzymes that catalyze hydrolysis of glycosidic bonds have identity numbers starting with E.C. 3.2. Enzymes that catalyze hydrolysis of peptide bonds have identity numbers starting with E.C. 3.4. Proteases, which are enzymes that catalyze hydrolysis of proteins, are classified using identity numbers starting with E.C. 3.4, including but not limited to Proteinase K and subtilisin. For example, Proteinase K has identity number E.C. 3.4.21.64. The present disclosure encompasses VLPs with capsids which are resistant, in non-limiting, example, Proteinase K, Protease from *Streptomyces griseus*, Protease from *Bacillus licheniformis*, pepsin and papain, and methods and processes of using such VLPs.

The Nomenclature Committee of the International Union of Biochemistry and Molecular Biology also recommends naming and classification of enzymes by the reactions they catalyze. Their complete recommendations are freely and widely available, and for example can be accessed online at http://enzyme.expasy.org and, www.chem.qmul.ac.uk/iubmb/enzyme/, among others. The IUBMB developed shorthand for describing what sites each enzyme is active against. Enzymes that indiscriminately cut are referred to as broadly specific. Some enzymes have more extensive binding requirements so the description can become more complicated. For an enzyme that catalyzes a very specific reaction, for example an enzyme that processes prothrombin to active thrombin, then that activity is the basis of the cleavage description. In certain instances the precise activity of an enzyme may not be clear, and in such cases, cleavage results against standard test proteins like B-chain insulin are reported.

The capsids can be further selected and/or prepared such that they can be isolated and purified using simple isolation and purification procedures, as described in further detail herein. For example, the capsids can be selected or genetically modified to have significantly higher hydrophobicity than a surrounding matrix as described herein, so as to selectively partition into a non-polar water-immiscible phase into which they are simply extracted. Alternatively, a capsid may be selected or genetically modified for improved ability to selectively crystallize from solution.

Use of simple and effective purification processes using the capsids is enabled by the choice of certain wild type capsids, or modifications to the amino acid sequence of capsid proteins comprising the wild type capsids, such that the capsid exhibits resistance to hydrolysis catalyzed by at least one hydrolase acting on peptide bonds as described herein above. Such wild type capsids, such as the wild type MS2 capsid, can be used in a purification process in which certain inexpensive enzymes such as Proteinase K or subtilisin are used for proteolysis. A non-limiting example is the Enterobacteria phage MS2 capsid protein, encoded by nucleic acid sequence SEQ ID NO: 2 producing amino acid sequence SEQ ID NO: 3. A non-limiting example is the Enterobacteria phage MS2 wild type genome (SEQ ID NO: 1) MS2 wild type coat protein DNA sequence (SEQ ID NO: 2); and MS2 wild type coat protein amino acid sequence (SEQ ID NO: 3).

Surprisingly, the unmodified, wild type MS2 capsid though lacking an envelope is resistant to a variety of category E.C. 3.4 hydrolases, including but not limited to Proteinase K and subtilisin, such that a highly purified VLP composition comprising the capsid, which may contain a cargo molecule, can be prepared from a whole cell lysate. Accordingly, the present disclosure provides VLPs comprising viral capsids comprising the wild type MS2 capsid protein, and/or capsid proteins sharing homology with wild type MS2 capsid proteins, which viral capsids encapsidate the cargo molecule. The cargo molecule may comprise one or more heterologous nucleic acids, peptides, polypeptides or proteins. These VLPs can then be isolated and purified from a whole cell lysate after a hydrolysis step using a category E.C. 3.4 hydrolase, to produce a composition of VLPs of high purity, for example at least 60%, at least 70%, a least 80%, or at least 85% by weight VLPs. Compositions having a purity of at least 90%, 91%, 92%, 93%, 94%, 95%, 96%, 97%, and 98% by weight of VLPs are expressly contemplated.

The present disclosure encompasses a composition comprising: a) a plurality of virus-like particles each comprising a wild type viral capsid and at least one target heterologous cargo molecule enclosed in the wild type viral capsid; and b) one or more cell lysis products present in an amount of less than 40 grams, less than 30 grams, less than 20 grams, less than 15 grams, less than 10 grams, and preferably less than 9, 8, 7, 6, 5, 4, 3, more preferably less than 2 grams, and still more preferably less than 1 gram, for every 100 grams of capsid present in the composition, wherein the cell lysis products are selected from proteins, polypeptides, peptides and any combination thereof. Subsequently the cargo molecules can be readily harvested from the capsids. Accordingly, such compositions are highly desirable for all applications where high purity and/or high production efficiency is required.

Hydrolase resistant capsids as described herein may be used to enclose different types of cargo molecules to form a virus-like particle. The cargo molecule can be but is not limited to any one or more oligonucleotide or oligoribonucleotide (DNA, RNA, LNA, PNA, siRNA, shRNA, sshRNA, lshRNA or miRNA, or any oligonucleotide comprising any type of non-naturally occurring nucleic acid), any peptide, polypeptide or protein. A cargo molecule which is an oligonucleotide or oligoribonucleotide may be enclosed in a capsid with or without the use of a linker. A capsid can be triggered for example to self-assemble from capsid protein in the presence of nucleotide cargo, such as an oligoribonucleotide. In non-limiting example, a capsid as described herein may enclose a target heterologous RNA strand, such as for example a target heterologous RNA strand containing a total of between 1,800 and 2,248 ribonucleotides, including the 19-mer pack site from Enterobacteria phage MS2, such RNA strand transcribed from a plasmid separate from a plasmid coding for the capsid proteins, as described by Wei, Y. et al. (2008) J. Clin. Microbiol. 46: 1734-1740.

RNA interference (RNAi) is a phenomenon mediated by short RNA molecules such as siRNA molecules, which can be used for selective suppression of a target gene of interest, and has multiple applications in biotechnology and medicine. For example, short RNA molecules can be employed to target a specific gene of interest in an organism to obtain a desirable phenotype. Short RNA molecules, including siRNA, are however easily degraded by ubiquitous enzymes called RNAses. Capsids, such as those described herein, protect encapsidated RNA from enzymatic degradation.

One or more RNA sequences can also be encapsidated into a viral capsid, either wild type or genetically modified, which has been modified to insert an external peptide tag, to deliver a protein or drug molecule to a specific class of cell. Wild type capsids may also be genetically modified to insert external peptide sequences acting as ligands for certain surface protein cell receptors can be advantageously used to encapsidate short RNA sequences aimed at inducing RNAi in specific target cells. Such compositions are much simpler, less expensive and more reliably manufactured than current alternatives for RNA delivery.

VLPs as described herein may alternatively enclose at least one target peptide, polypeptide or protein within a capsid. When the target heterologous cargo molecule is a peptide, polypeptide or protein, an oligonucleotide linker can be used to couple the target heterologous cargo molecule and the viral capsid. A cargo molecule which is a peptide, polypeptide or protein, preferably is packaged in a capsid using a linker. The packaging process is promoted by the linker, consisting of a short RNA aptamer sequence, which forms a link between the coat protein and a peptide tag fused to the target cargo molecule. (See Fiedler, J. et al, RNA-Directed Packaging of Enzymes within Virus-like Particles, Angew. Chem. Int. Ed. 49: 9648-9651 (2010)). The oligonucleotide linker may consist of DNA, RNA, LNA, PNA, and the like. The linker is for example a 50- to 100-mer having a short sequence, for example about 20 nt long, at a first end with binding specificity for the inside of the capsid coat, and another sequence, for example about 70 nt long, at the second, opposite end which has a binding specificity for the cargo peptide, polypeptide or protein. Alternatively, a capsid as described herein may enclose at least one target protein N-terminally tagged with a peptide able to non-covalently bind to an aptamer- and capsid pack sequence-containing RNA strand, for example an N-terminal tag and aptamer- and pack sequence-containing RNA strand as described by Fiedler, J. et al. (2010).

VLPs as described herein may be assembled by any available method(s) which produces a VLP with an assembled, hydrolase resistant capsid encapsidating one or more cargo molecule(s). For example, capsids and cargo molecules may be co-expressed in any expression system. Recombinant DNA encoding one or more capsid proteins, one or more cargo molecule(s) can be readily introduced into the host cells, e.g., bacterial cells, plant cells, yeast cells, fungal cells, and animal cells (including insect and mammalian) by transfection with one or more expression vectors by any procedure useful for introducing such a vector into a particular cell, and stably transfecting the cell to yield a cell which expresses the recombinant sequence(s).

The host cell is preferably of eukaryotic origin, e.g., plant, mammalian, insect, yeast or fungal sources, but non-eukaryotic host cells may also be used. Suitable expression systems include but are not limited to microorganisms such as bacteria {e.g., *E. coli*) transformed with recombinant bacteriophage DNA, plasmid DNA or cosmid DNA expression vectors containing the coding sequences for the VLP elements. In non-limiting example, for VLPs using the MS2 capsid protein, expression in *E. coli* is a suitable expression system.

The present disclosure expressly contemplates plant cells which have been transformed using a nucleic acid construct as described herein, and which expresses a capsid coat protein and cargo molecule. Means for transforming cells including plant cells and preparing transgenic cells are well known in the art. Vectors, plasmids, cosmids, YACs (yeast artificial chromosomes) and DNA segments can be used to transform cells and will as generally recognized include promoters, enhancers, and/or polylinkers. Transgenic cells specifically contemplated include transgenic plant cells including but not limited to cells obtained from corn, soybean, wheat, vegetables, grains, legumes, fruit trees, and so on, or any plant which would benefit from introduction of a VLP as described herein. Also contemplated are plants, plant tissue obtained from cells transformed as described herein, and the seed or progeny of the plant or plant tissue.

Expression of assembled VLPs can be obtained for example by constructing at least one expression vector including sequences encoding all elements of the VLP. Sometimes two vectors are used, a first vector which includes a sequence encoding the cargo molecule(s); and a second vector which includes a sequence encoding the capsid protein. In an exemplary process for generating exemplary VLPs including siRNA, two vectors may be co-expressed in the host cell for generation of the VLP, as further detailed in the Examples. Methods and tools for constructing such expression vectors containing the coding sequences and transcriptional and translational control sequences are well known in the art. Vector(s) once constructed are transferred to the host cells also using techniques well known in the art, and the cells then maintained under culture conditions for a time sufficient for expression and assembling of the VLP's to occur, all using conventional techniques. The present disclosure thus encompasses host cells containing any such vectors, and cells which have been transformed by such vectors, as well as cells containing the VLP's.

When the VLP's have been expressed and assembled in the host cell they may be isolated and purified using any method known in the art for virus purification. For example, the cells can be lysed using conventional cell lysis techniques and agents, and the cell lysate subjected to hydrolysis using at least one peptide bond hydrolase category E.C. 3.4 such as but not limited to Proteinase K or subtilisin. Intact capsids remaining in the cell lysate following hydrolysis can be removed and purified using conventional protein isolation techniques.

Purification of capsids, VLPs or proteins may also include methods generally known in the art. For example, following capsid expression and cell lysis, the resulting lysate can be subjected to one or more isolation or purification steps. Such steps may include for example enzymatic lipolysis, DNA hydrolysis, and proteolysis steps. A proteolysis step may be performed for example using a blend of endo- and exo-proteases. For example, after cell lysis and hydrolytic disassembly of most cell components, such capsids with their cargo molecules can be separated from surrounding matrix by extraction, for example into a suitable non-polar water-immiscible solvent, or by crystallization from a suitable solvent. For example, hydrolysis and/or proteolysis steps transform contaminants from the capsid that are contained in the lysate matrix into small, water soluble molecules. Hydrophobic capsids may then be extracted into an organic phase such as 1,3-bis(trifluoromethyl)benzene. Purification of capsids, VLPs or proteins may include for example at least one liquid-liquid extraction step, at least one fractional precipitation step, at least one ultrafiltration step, or at least one crystallization step. A liquid-liquid extraction may comprise for example use of an immiscible non-aqueous non-polar solvent, such as but not limited to benzene, toluene, hexane, heptane, octane, chloroform, dichloromethane, or carbon tetrachloride. Purifying may include at least one crystallization step. Use of one or more hydrolytic steps, and especially of one or more proteolytic steps, eliminates certain problems observed with current separation processes used for cargo molecules, which are mainly result from the large number and varying degree of binding interactions which take place between cargo molecules and components derived from the cell culture in which they are produced. The capsids described herein resist hydrolytic steps such that the matrix which results after hydrolysis includes intact capsids which safely partition any cargo molecules from the surrounding matrix, thereby interrupting the troublesome binding interactions which interfere with current purification processes.

Following purification, the capsid can be opened to obtain the cargo molecule, which maybe a protein or polypeptide, a peptide, or a nucleic acid molecule as described herein. Capsids can be opened using any one of several possible procedures known in the art, including for example heating in an aqueous solution above 50° C.; repeated freeze-thawing; incubating with denaturing agents such as formamide; or by a combination of any of these procedures.

Capsids which are resistant to hydrolases and useful in the VLPs and methods according to the present disclosure can also be variants of, or derived from the wild type MS2 capsid. Capsid proteins may comprise, for example, at least one substitution, deletion or insertion of an amino acid residue relative to the wild type MS2 capsid protein amino acid sequence. Such capsid proteins may be naturally occurring variants or can be obtained by genetically modifying the MS2 capsid protein using conventional techniques, provided that the variant or modified capsid protein forms a non-enveloped capsid which is resistant to hydolysis catalyzed by a peptide bond hydrolase category E.C. 3.4 as described herein.

Genetically modified MS2 capsid proteins which can assemble into capsids which are resistant to hydrolysis as described herein can be engineered by making select modifications in the amino acid sequence according to conventional and well-known principles in physical chemistry and biochemistry as described herein and in the Examples herein below.

It is common knowledge for example that the shape or global fold of a functional protein is determined by the amino acid sequence of the protein, and that the fold defines the protein's function. The global fold is comprised of one or more folding domains. When more than one folding domain exists in the global fold, the domains generally bind together, loosely or tightly along a domain interface. The domain fold can be broken down into a folding core of tightly packed, well-defined secondary structure elements which is primarily responsible for the domain's shape and a more mobile outer layer typically comprised of turns and loops whose conformations are influenced by interactions with the folding core as well as interactions with nearby domains and other molecules, including solvent and other proteins. An extensive public domain database of protein folds, the Structural Classification of Proteins (SCOP) database (Alexey G Murzin, Curr Opin Struct Biol (1996) 6, 386-394) of solved protein structures in the public domain is maintained online at http://scop.berkeley.edu and regularly expanded as new solved structures enter the public domain (Protein Data Bank (F. C. Bernstein, T. F. Koetzle, G. J. Williams, E. E. Meyer Jr., M. D. Brice, J. R. Rodgers, O. Kennard, T. Shimanouchi, M. Tasumi, "The Protein Data Bank: A Computer-based Archival File For Macromolecular Structures," J. of. Mol. Biol, 112 (1977): 535), http://www.rcsb.org) database. Members of a family which are evolutionarily distant, yet have the same shape and very similar function, commonly retain as few as 30% identical residues at topologically and/or functionally equivalent positions. In some families, sequences of distant members have as few as 20% of their residues unchanged with respect to each other, e.g. levi- and alloleviviridae capsid proteins. Further, the fold and function of a protein is remarkably tolerant to change via directed or random mutation, even of core residues (Peter O. Olins, S. Christopher Bauer, Sarah Braford-Goldberg, Kris Sterbenz, Joseph O. Polazzi, Maire H. Caparon, Barbara K. Klein, Alan M. Easton, Kumnan Paik, Jon A. Klover, Barrett R. Thiele, and John P. McKearn (1995) J Biol Chem 270, 23754-23760; Yiqing Feng, Barbara K. Klein and Charles A. McWherter (1996), J Mol Biol 259, 524-541; Dale Rennell, Suzanne E. Bouvier, Larry W. Hardy and Anthony R. Poteetel (1991) J Mol Biol 222, 67-87), insertion/deletion of one or more residues (Yiqing Feng, Barbara K. Klein and Charles A. McWherter (1996), J Mol Biol 259, 524-541), permutation of the sequence (Multi-functional chimeric hematopoietic fusion proteins between sequence rearranged c-mpl receptor agonists and other hematopoietic factors, U.S. Pat. No. 6,066,318), concatenation via the N- or C-terminus or both (to copies of itself or other peptides or proteins) (Multi-functional chimeric hematopoietic fusion proteins between sequence rearranged g-csf receptor agonists and other hematopoietic factors, US20040171115; Plevka, P., Tars, K., Liljas, L. (2008) Protein Sci. 17: 173) or covalent modification, e.g., glycosylation, pegylation, SUMOylation or the addition of peptidyl or nonpeptidyl affinity tags as long as the residues critical to maintaining the fold and/or function are spared.

VLPs according to the present disclosure and as used in any of the methods and processes, thus encompass those comprising a capsid protein having at least 15%, 16%, 21%, 40%, 41%, 52%, 53%, 56%, 59% or at least 86% sequence identity with the amino acid sequence of wild type Enterobacteria phage MS2 capsid protein (SEQ ID NO: 3). Such VLPs include for example a VLP comprising a capsid protein having at least 52% sequence identity with SEQ ID NO: 3 as described above. Also included is a VLP comprising a capsid protein having at least 53% sequence identity to SEQ ID NO:3, which can be obtained substantially as described above but not disregarding the FR capsid sequence, representing 53% sequence identity to wild-type enterobacteria phage MS2 capsid protein (SEQ ID NO:3). Also included is a VLP comprising a capsid protein having at least 56% sequence identity to SEQ ID NO:3, when it is considered that when the structures identified as 1AQ3 (van den Worm, S. H., Stonehouse, N. J., Valegard, K., Murray, J. B., Walton, C, Fridborg, K., Stockley, P. G., Liljas, L. (1998) Nucleic Acids Res. 26: 1345-1351), 1GAV (Tars, K., Bundule, M., Fridborg, K., Liljas, L. (1997) J. Mol. Biol. 271: 759-773), 1FRS (Liljas, L., Fridborg, K., Valegard, K., Bundule, M., Pumpens, P. (1994) J. Mol. Biol. 244: 279-290) and 2VTU (Plevka, P., Tars, K., Liljas, L. (2008) Protein Sci. 17: 1731) (Protein Data Bank identifiers described above), only 56% of the sequence positions have identical sequence and topologically equivalent positions with respect to the backbone overlays when all three sequences are considered together. Also included is a VLP comprising a capsid protein having at least 59% sequence identity to SEQ ID NO:3, when it is considered that the sequence of the MS2 viral capsid protein compared to that of the GA viral capsid protein is 59%. Also included is a VLP comprising a capsid protein having at least 86% sequence identity to SEQ ID NO:3, when it is considered that the sequence of the MS2 viral capsid protein compared to that of the FR capsid protein is 86%. VLPs according to the present disclosure thus encompass those comprising a capsid protein having at least 15%, 16%, or 21% sequence identity with the amino acid sequence of wild type Enterobacteria phage MS2 capsid (SEQ ID NO:3) based on a valid structure anchored alignment.

A VLP may thus comprise any of the MS2 capsid protein variants as described herein. Genetically modified capsid proteins consistent with those described herein can be produced for example by constructing at least one DNA plasmid encoding at least one capsid protein having at least one amino acid substitution, deletion or insertion relative to the amino acid sequence of the wild type MS2 capsid protein, making multiple copies of each plasmid, transforming a cell line with the plasmids; maintaining the cells for a time and under conditions sufficient for the transformed cells to express and assemble capsids encapsidating nucleic acids; lysing the cells to form a cell lysate; subjecting the cell lysate to hydrolysis using at least one peptide bond hydrolase, category E.C. 3.4; and removing intact capsids remaining in the cell lysate following hydrolysis to obtain capsids having increased resistance to at least one hydrolase relative to the wild type capsid protein. Following purification of the resulting, intact capsids, an amino acid sequence for each capsid protein may be determined according to methods known in the art.

The specialized capsids described herein can be used in research and development and in industrial manufacturing facilities to provide improved yields, since the purification processes used in both settings have the same matrix composition. Having such same composition mainly depends on using the same cell line in both research and development and manufacturing processes. However, differences in matrix composition due to using different cell lines are greatly reduced after proteolytic steps used in both research and development and manufacturing stages. This feature enables use of different cell lines in both stages with a minimal manufacturing yield penalty.

EXAMPLES

The following non-limiting examples are included to illustrate various aspects of the present disclosure. It will be appreciated by those of skill in the art that the techniques disclosed in the following examples represent techniques discovered by the Applicants to function well in the practice of the invention, and thus can be considered to constitute preferred modes for its practice. However, those of skill in the art should, in light of the instant disclosure, appreciate that many changes can be made in the specific examples described, while still obtaining like or similar results, without departing from the scope of the invention. Thus, the examples are exemplary only and should not be construed to limit the invention in any way. To the extent necessary to enable and describe the instant invention, all references cited are herein incorporated by reference.

Example A

Propagation of MS2 Bacteriophage

Figure 1:
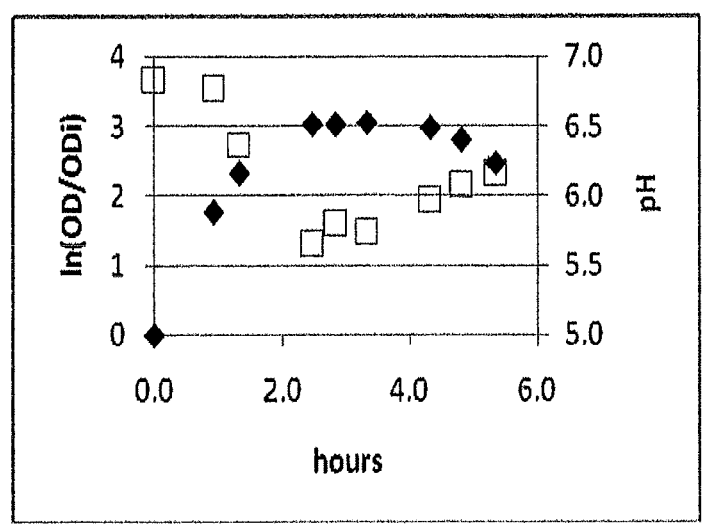
FIG. 1 is a plot of Optical Density (OD; filled diamonds) and pH (open squares) over time, showing propagation of wild type MS2 bacteriophage (ATCC No. 15597-B1, from American Type Culture Collection, Rockville, Md.) in its *E. coli* host (ATCC No. 15669).

MS2 bacteriophage (ATCC No. 15597-B 1, from American Type Culture Collection, Rockville, Md.) and its *E. coli* host (ATCC No. 15669) were obtained from ATCC and propagated using the procedure described by Strauss and Sinsheimer (1963) J. Mol. Biol 7:43-54 J. Mol. Biol 7:43-54. Results are plotted in FIG. 1. Optical Density (OD) at 600 nm and pH were followed during the reaction. ODi represents OD immediately after inoculation with host. Infection was done at 2.3 hours. Ln(OD/ODi) was plotted on the left axis (full diamonds) and pH was plotted on the right axis (open squares). This experiment was ended 5.3 hours after inoculation with host. Lysate obtained was centrifuged at 2,000 g and filtered through a 0.2 μm membrane to eliminate remaining bacteria and bacterial debris.

Example B

Purification of MS2 Bacteriophage Using Proteinase K and Ultrafiltration

Figure 2:
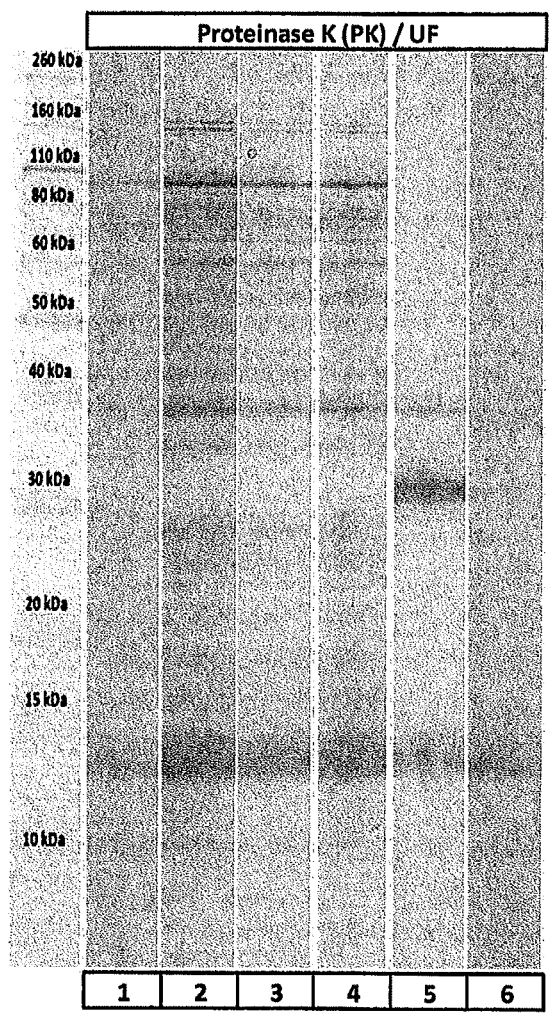
FIG. 2 is a gel showing results of SDS-PAGE analysis of MS2 bacteriophage samples obtained following propagation in *E. coli* and purified using Proteinase K and ultrafiltration, showing that Proteinase K purification yields phage purified to higher than 99% (band at 14 kDa corresponds to MS2 bacteriophage coat protein).

Purification of MS2 bacteriophage was conducted as follows. Samples were taken during purification and SDS PAGE analysis was run on the samples. Results obtained are shown in FIG. 2. Eight milliliters of lysate obtained at end of Example A (sample in Lane 1, FIG. 2) was filtered through a 300 kDa membrane (Vivaspin 2, from Sartorius Stedim, Bohemia, N.Y.) and the filtrate was filtered through a 100 kDa membrane, from which 1 mL of retentate was obtained (sample in Lane 2, FIG. 2). This retentate was divided in two equal parts. To one half (control) 206 μL, 20 mM $CaCl_2$ aqueous solution at pH=7.5 were added. To the second half (Proteinase) 0.15 mg Proteinase K (Sigma Aldrich, St. Louis, Mo.) dissolved in 206 μL, 20 mM $CaCl_2$ aqueous solution at pH=7.5 was added. Both tubes were incubated at 37° C. and after 1 hour they were placed in an ice-water bath. Samples were then taken and analyzed: control sample in Lane 3, FIG. 2, and Proteinase sample in Lane 5, FIG. 2. Each product was then diluted to 2 mL with deionized (DI) water and filtered through a 100 kDa membrane. Each retentate (150 μL) was diluted to 2 mL with DI water and filtered again through the same membrane. Dilution and ultrafiltration was repeated one more time for each product. Samples of each retentate were then taken and analyzed: control sample in Lane 4, FIG. 2, and Proteinase sample in Lane 6, FIG. 2. Band at 14 kDa corresponds to MS2 bacteriophage's coat protein. Band at 30 kDa corresponds to Proteinase K. Product from control experiment yields a highly impure phage. Product from the Proteinase experiment yields a product containing phage with purity higher than 99%.

Example C

Degradation of MS2 Bacteriophage

Figure 3:
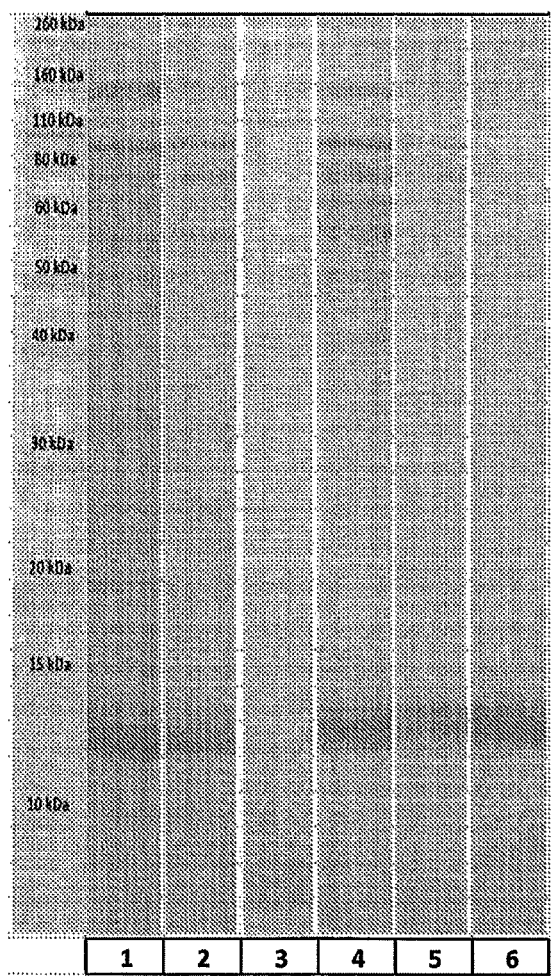
FIG. 3 is a gel showing results of SDS-PAGE analysis of partially purified MS2, showing complete degradation of the phage and results obtained after 1× or 2× ultrafiltration of the lysate (Lanes 4 and 6).

Treatment of MS2 bacteriophage was conducted as follows. Samples were taken during treatment and SDS PAGE analysis was run on the samples. Results obtained are shown in FIG. 3. Four milliliters of lysate obtained at end of Example A was partially purified by precipitation using ammonium sulfate and extraction using trichlorofluoromethane (Freon 11) as described by Strauss & Sinsheimer (1963) J. Mol. Biol 7:43-54. A sample of the aqueous solution after extraction with Freon 11 was taken and analyzed (sample in Lane 1, FIG. 3). To the partially purified phage solution (130 μL) 370 μL, of 20 mM $CaCl_2$ aqueous solution was added. The mixture was incubated at 37° C. and after 1 hour it was placed in an ice-water bath. A sample was then taken and analyzed: sample in Lane 2, FIG. 3. The incubation product was diluted to 2 mL with deionized (DI) water and filtered through a 100 kDa membrane. The retentate (150 μL) was diluted to 2 mL with DI water and filtered again through the same membrane. Dilution and ultrafiltration of the retentate was repeated one more time. A sample of the retentate was then taken and analyzed: sample in Lane 3, FIG. 3. Only weak bands at lower than 10 kDa were observed, indicating complete degradation of phage.

Example D

Purification of MS2 Bacteriophage Using Ultrafiltration

Purification of MS2 bacteriophage was conducted as follows. Samples were taken during purification and SDS PAGE analysis was run on the samples. Results obtained are shown in FIG. 3. Four milliliters of lysate obtained at end of Example A was partially purified by precipitation using ammonium sulfate and extraction using trichlorofluoromethane (Freon 11) as described by Strauss & Sinsheimer (1963) J. Mol. Biol 7:43-54. The aqueous solution containing partially purified phage was diluted to 2 mL with deionized water, filtered through a 300 kDa membrane and the filtrate was filtered through a 100 kDa membrane, from which 150 μl of retentate was obtained. The retentate was then diluted to 2 mL with deionized (DI) water and filtered through the same 100 kDa membrane. Dilution and ultrafiltration of the retentate (150 μL) was repeated one more time. A sample of the retentate was then taken and analyzed: sample in Lane 4, FIG. 3. 370 μL of 20 mM $CaCl_2$ aqueous solution was added to the retentate (130 μL). The mixture was incubated at 37° C. and after 1 hour it was placed in an ice-water bath. A sample was then taken and analyzed: sample in Lane 5, FIG. 3. The product was then diluted to 2 mL with deionized (DI) water and filtered through a 100 kDa membrane. The retentate (150 μL) was diluted to 2 mL with DI water and filtered again through the same membrane. Dilution and ultrafiltration of the retentate was repeated one more time. A sample of the retentate was then taken and analyzed: sample in Lane 6, FIG. 3. MS2's capsid protein, of 14 kDa, retained by a membrane through which permeate proteins with less than 100 kDa molecular weight is clearly visible, indicating the presence of intact MS2 capsids. The product obtained contained phage with purity higher than 99%.

Example E

Purification of MS2 Bacteriophage Using Proteinase K and Ultrafiltration

Figure 4:
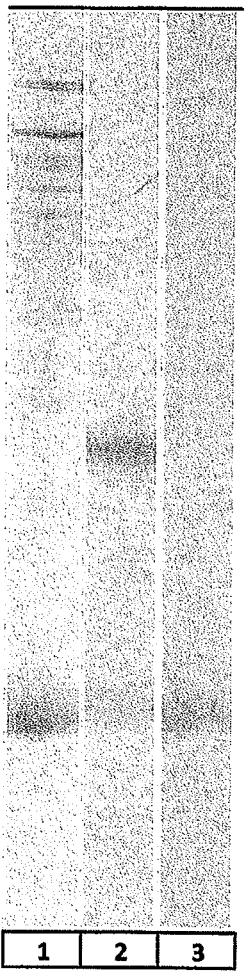
FIG. 4 is a gel showing results of SDS-PAGE analysis of MS2 samples purified using ultrafiltration and Proteinase K treatment.

Purification of MS2 bacteriophage was conducted as follows. Samples were taken during purification and SDS PAGE analysis was run on the samples. Results obtained are shown in FIG. 4. Four milliliters of lysate obtained at end of Example A was partially purified by precipitation using ammonium sulfate and extraction using trichlorofluoromethane (Freon 11) as described by Strauss & Sinsheimer (1963) J. Mol. Biol 7:43-54. The aqueous solution containing partially purified phage was diluted to 2 mL with deionized water, filtered through a 100 kDa membrane, from which 150 μL of retentate was obtained. The retentate was then diluted to 2 mL with deionized (DI) water and filtered through the same 100 kDa membrane. Dilution and ultrafiltration of the retentate (150 μL) was repeated one more time. A sample of the retentate was then taken and analyzed: sample in Lane 1, FIG. 4. 0.15 mg of Proteinase K dissolved in 370 μL of 20 mM CaCl$_2$ aqueous solution was added to the retentate (130 μL). The mixture was incubated at 37° C. and after 1 hour it was placed in an ice-water bath. A sample was then taken and analyzed: sample in Lane 2, FIG. 4. The product was then diluted to 2 mL with deionized (DI) water and filtered through a 100 kDa membrane. The retentate (150 μL) was diluted to 2 mL with DI water and filtered again through the same membrane. Dilution and ultrafiltration of the retentate was repeated one more time. A sample of the retentate was then taken and analyzed: sample in Lane 3, FIG. 4. The product obtained contained phage with purity higher than 99%.

Example F

Figure 5:
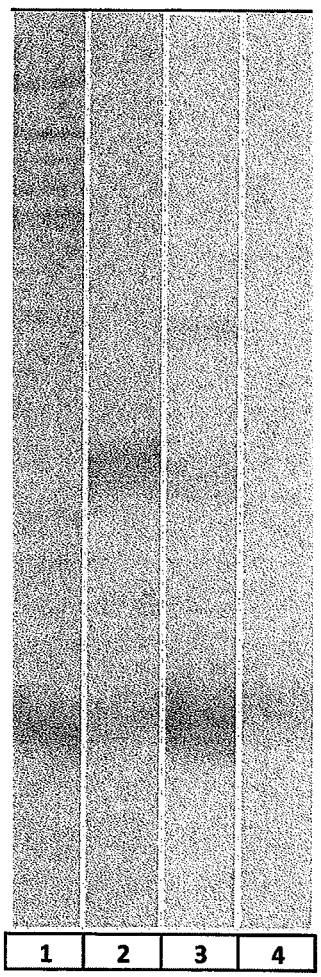
FIG. 5 is a gel showing results of SDS-PAGE analysis of MS2 samples purified using Proteinase K treatment, precipitation at acidic conditions, precipitation using ethanol at basic and acidic conditions, and ultrafiltration.
Figure 6:
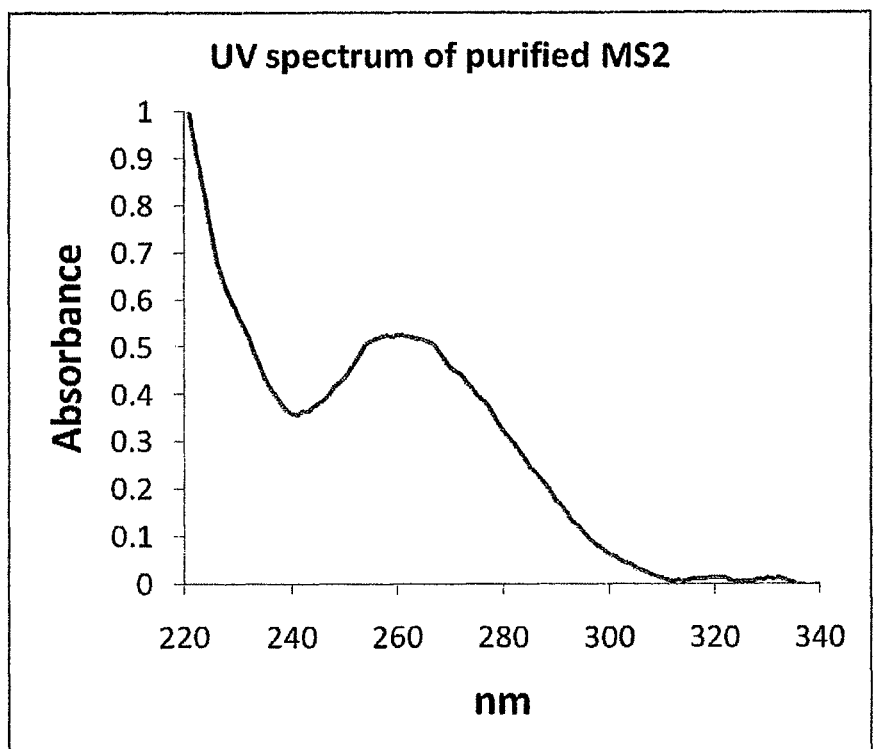
FIG. 6 is a graph showing the UV spectrum of MS2 samples purified using Proteinase K treatment, precipitation at acidic conditions, precipitation using ethanol at basic and acidic conditions, and ultrafiltration.
Figure 7:
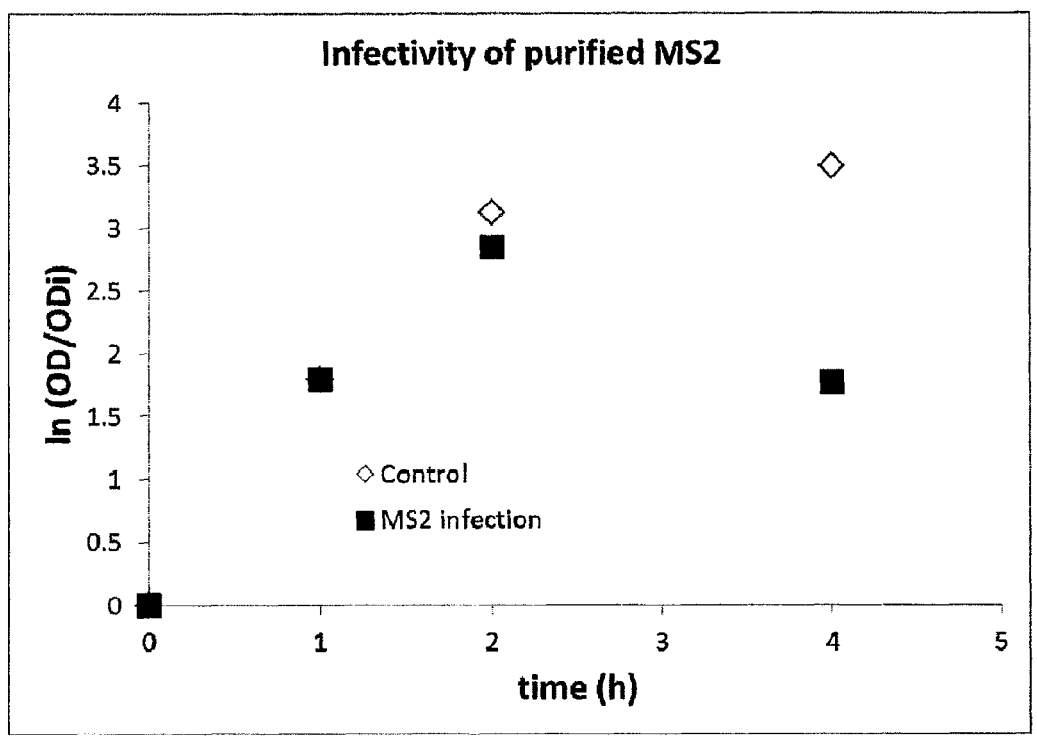
FIG. 7 is a plot of Optical Density (OD; filled diamonds) over time, obtained with a control sample (open diamonds) and an MS2 sample following purification described for FIGS. 5 and 6 (filled squares), showing that the purified sample contained phage that retained high infectivity.

Purification of MS2 Bacteriophage Using Proteinase K, Precipitation at Acidic Conditions, Precipitation Using Ethanol at Basic and Acidic Conditions, and Ultrafiltration Purification of MS2 bacteriophage was conducted as follows. Samples were taken during purification and SDS PAGE analysis was run on the samples. Results obtained are shown in FIG. 5. Fifty milliliters of lysate obtained at end of Example A was partially purified by precipitation using ammonium sulfate and extraction using trichlorofluoromethane (Freon 11) as described by Strauss & Sinsheimer (1963) J. Mol. Biol 7:43-54. A sample of the aqueous solution after extraction with Freon 11 was taken and analyzed (sample in Lane 1, FIG. 5). To the partially purified phage solution (1.2 mL) 0.9 mg of Proteinase K dissolved in 1.24 mL of 20 mM CaCl$_2$ aqueous solution was added. The mixture was incubated at 37° C. and after 1 hour 60 μL of 0.2M Phenylmethanesulfonyl fluoride (PMSF) solution in ethanol was added to inactivate Proteinase K. The mixture was then placed in an ice-water bath. A sample was taken and analyzed: sample in Lane 2, FIG. 5.0. Six hundred and eighty microliters of 0.1% phosphoric acid aqueous solution was slowly added with vigorous agitation in an ice/water bath to bring the pH of the liquid to 4. The liquid was kept at 0° C. for 30 minutes and centrifuged at 16,000 g at 4° C. for 30 min. The supernatant was allowed to reach room temperature and 130 μL of 1% NaOH was added to bring the pH of the liquid to 8. 0.81 mL of ethanol at room temperature was slowly added with vigorous agitation to bring the ethanol concentration in the liquid to 20%. The liquid was kept at room temperature for 30 min and centrifuged at 16,000 g at room temperature for 30 min. The supernatant was placed in an ice/water bath for 15 min and 1.3 mL of 1% acetic acid was slowly added at 0° C. with vigorous agitation to bring the pH of the liquid to 4. 1.5 mL of ethanol at 0° C. was slowly added with vigorous agitation to bring the ethanol concentration in the liquid to 34%. The liquid was kept at 0° C. for 30 minutes and centrifuged at 16,000 g at 4° C. for 30 min. The pellet was resuspended in 200 μL of DI water and a 20 μL sample was taken and analyzed: Lane 3, FIG. 5. The rest (180 μL) was diluted with DI water to 2 mL and filtered through 100 kDa membrane. The retentate (150 μL) was diluted to 2 mL with DI water and filtered again through the same membrane. Dilution and ultrafiltration of the retentate was repeated one more time. A sample of the retentate was then taken and analyzed by SDS PAGE: sample in Lane 4, FIG. 5. MS2's coat protein, of 14 kDa, retained by a membrane through which proteins with less than 100 kDa molecular weight are able to permeate, is clearly visible, consistent with the presence of intact MS2 capsids. A UV spectrum on the same retentate is shown in FIG. 6, which is consistent with results published by G. F. Rohrmann and R. G. Krueger, (1970) J. Virol, 6(3):26 for pure MS2 phage. A Superdex 200 (GE Healthcare, Piscataway, N.J.) size exclusion chromatography was run on the same retentate using Tris-buffered saline at pH 7.4 and 150 mM NaCl. It showed 280 nm absorbance only at the void volume of the column. There was no absorbance in the elution volume for proteins of 600 kDa to 2 kDa. This test is consistent with intact phage particles. RNA was isolated from another sample of the same retentate using a QIAamp Viral RNA Mini Kit (Qiagen, Valencia, Calif.) and a DNA-free kit (Life Technologies, Grand Island, N.Y.), and reverse transcribed using a High Capacity cDNA Reverse Transcription Kit (Life Technologies). The presence or absence of three different sections of the MS2 genome was then interrogated in PCR experiments. The following pairs of primers were used, each primer named for the position of its first and last base in the MS2 genome, forward (F) and reverse (R) respectively: F1001__1021-R2180__2201, F1201__1223-R1979__2001, F1401__1426-R1680__1705. Platinum Taq DNA Polymerase High Fidelity (Life Technologies) was used for amplification. PCR products, analyzed in 1.5% agarose gel stained with Ethidium Bromide, as shown in FIG. 9 (1.2 kbp for primers F1201__1223-R1979__2001 in Lane 1, 800 bp for primers F1201__1223-R1979__2001 in Lane 2, and 304 bp for primers F1401__1426-R1680__1705 in Lane 3), were consistent with an intact MS2 bacteriophage genome. An infectivity test was also run on the same retentate as follows. Five microliters of retentate were used to infect 1 mL of bacterial culture as described in Example A at the point it reached OD (600 nm)=0.22. OD (600 nm) was 0.82 1 hour after infection and dropped to 0.21 after 2 additional hours, while during the same time a control sample attained OD (600 nm) of 0.82 1 hour after infection and 1.2 after 2 additional hours, as shown in FIG. 7. This test showed a highly infectious phage in the retentate and therefore demonstrated that the purification processes used to isolate it did not compromise its integrity. In conclusion, the product obtained contained MS2 bacteriophage with purity higher than 99%.

Example G

Purification of MS2 Bacteriophage Using Different Exogenous Proteases, and Ultrafiltration Purification of MS2 bacteriophage using different exogenous proteases was attempted substantially as described in Example E, with the exception that proteases other than Proteinase K were used. MS2 bacteriophage was successfully purified after proteolysis promoted by Protease from *Bacillus licheniformis* (P5380, Sigma Aldrich). However, a proteolysis reaction using Pepsin from porcine gastric mucosa (P6887, Sigma Aldrich) at pH of 6 was found to significantly degrade MS2 bacteriophage. On the other hand, proteolysis reactions using Papain from papaya latex (P3125, Sigma Aldrich) at pH 6 did not extensively degrade MS2 bacteriophage.

Example H

Figure 8:
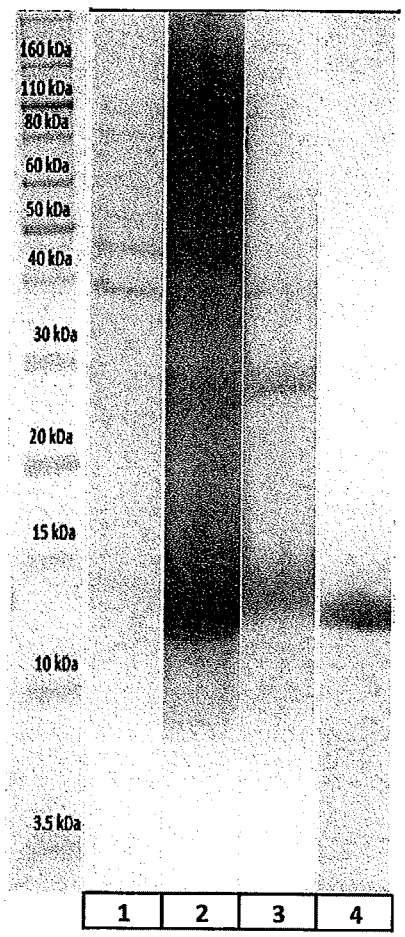
FIG. 8 is a gel showing results of SDS-PAGE analysis of VLP samples following expression of MS2 capsids encapsidating RNA coding for the capsid protein attached to a coat-specific 19-mer RNA hairpin.

Production of VLP Capsids Encapsidating RNA Coding for MS2 Capsid Protein Attached to its Specific 19-Mer RNA Hairpin Production of VLP capsids was conducted as follows. Samples were taken during the course of expression and SDS PAGE analysis was run on the samples to monitor capsid production. Results obtained are shown in FIG. 8. A DNA sequence, SEQ ID NO: 4, encoding MS2's capsid protein and its specific RNA 19-mer PAC site was cloned into pDEST14 A252 plasmid (Life Technologies).

One Shot BL21(DE3) Chemically Competent *E. coli* (Life Technologies) cells were transformed using such plasmid. BL21(DE3) containing the plasmid were grown in 750 mL of LB medium containing ampicillin at 37° C., to OD (600 nm) equal to 0.8. A pre-induction sample was then taken and analyzed: sample in Lane 1, FIG. 8. Isopropyl β-D-1-thiogalactopyranoside (Sigma-Aldrich) was then added to a final concentration of 1 mM. Four hours post-induction cells were harvested by centrifugation at 3,000 g and 4° C. for 40 min. A sample was then taken and analyzed: sample in Lane 2, FIG. 8.

Example I

Purification and Characterization of VLP Capsids Encapsidating RNA Coding for MS2 Capsid Protein Attached to its Specific 19-Mer RNA Hairpin Purification of VLP capsids was conducted as follows. Samples were taken during purification and SDS PAGE analysis was run on the samples. Results obtained are shown in FIG. 8. A fraction of the pellet from Example H equivalent to 115 mL of culture was resuspended in 20 mM Tris-HCl, pH 7.5, containing 10 mM $MgCl_2$ and sonicated to lyse cells. Cell debris was removed by centrifugation at 16,000 g. The cell lysate obtained was partially purified by precipitation using ammonium sulfate and extraction using trichlorofluoromethane (Freon 11) as described by Strauss & Sinsheimer (1963) J. Mol. Biol 7:43-54. To the partially purified VLP capsid solution (1.05 mL) 0.3 mg of Proteinase K dissolved in 1.05 mL of 20 mM $CaCl_2$ aqueous solution was added. The mixture was incubated at 37° C. and after 2.5 hours it was placed in an ice-water bath. A sample was then taken and analyzed: sample in Lane 3, FIG. 8. Fifteen minutes afterwards, 0.14 mL of 1% phosphoric acid aqueous solution was slowly added with vigorous agitation in an ice/water bath to bring the pH of the liquid to 4.1. The liquid was kept at 0° C. for 30 minutes and centrifuged at 16,000 g at 4° C. for 20 min. To the supernatant, kept at 0° C., 100 μL, of 1% NaOH was added to bring the pH of the liquid to 7.9. Five hundred microliters of ethanol at 0° C. was then slowly added with vigorous agitation to bring the ethanol concentration in the liquid to 20%. The liquid was kept at 0° C. for 30 minutes and centrifuged at 16,000 g at 4° C. for 20 min. After adding 1% acetic acid to adjust the pH of the solution to 7, the supernatant was filtered through a Vivaspin 2 (Sartorius) 300 kDa membrane and the filtrate was filtered through a 100 kDa membrane, from which 150 μL of retentate was obtained. The retentate was then diluted to 2 mL with phosphate buffered saline and filtered through the same 100 kDa membrane. Dilution and ultrafiltration of the retentate (150 μL) was repeated four more times. A sample of the retentate was then taken and analyzed by SDS PAGE: sample in Lane 4, FIG. 8. MS2's capsid protein, of 14 kDa, retained by a membrane through which proteins with less than 100 kDa molecular weight are able to permeate, is clearly visible, consistent with the presence of intact VLP capsids. RNA was isolated from another sample of the same retentate using a QIAamp Viral RNA Mini Kit (Qiagen, Valencia, Calif.) and a DNA-free kit (Life Technologies, Grand Island, N.Y.), and reverse transcribed using a High Capacity cDNA Reverse Transcription Kit (Life Technologies). The presence or absence of a section of the MS2 capsid protein was then interrogated in PCR experiments. The following pair of primers was used, each primer named for the position of its first and last base in the MS2 genome, forward (F) and reverse (R) respectively: F1401_1426-R1680_1705. Platinum Taq DNA Polymerase High Fidelity (Life Technologies) was used for amplification. The PCR product, analyzed in 2% agarose gel stained with Ethidium Bromide, as shown in FIG. 10 (304 bp in Lane 1; the leftmost Lane corresponds to 1 kb plus ladder from Life Technologies), was consistent with an intact MS2 capsid gene. In conclusion, the product obtained contained VLP capsids with purity higher than 99%.

Example J

Simple Precipitation with Ethanol for Purification of VLPs

Purification of VLPs was conducted as follows. Samples were taken during purification and SDS PAGE analysis was run on the samples. Results obtained are shown in FIG. 11. One sixth of the pellet obtained from an experiment identical to Example H was resuspended in 20 mM Tris-HCl, pH 7.5, containing 10 mM $MgCl_2$ and sonicated to lyse cells. Cell debris was removed by centrifugation at 16,000 g. The cell lysate obtained was partially purified by precipitation using ammonium sulfate and extraction using trichlorofluoromethane (Freon 11) as described by Strauss & Sinsheimer (1963) J. Mol. Biol 7:43-54. A sample was taken and analyzed: sample in Lane 1, FIG. 11. A strong band at about 14 kDa was found, consistent with the capsid protein of MS2 phage. Other bands—impurities—mostly of higher molecular weight, represent about 27% of the sample weight. To the partially purified MS2 VLP solution (1.35 mL) 1.36 mL of 20 mM $CaCl_2$ aqueous solution was added and placed in an ice-water bath. Fifteen minutes afterwards, 50 µL of 10% acetic acid aqueous solution was added to bring the pH of the liquid to 4.1. Then, at the same temperature and with vigorous agitation, 1.44 mL of ethanol was slowly added. The liquid was kept at 0° C. for 30 minutes and centrifuged at 16,000 g at 4° C. for 20 min. The pellet was suspended in 2 mL of an aqueous buffer consisting of 20 mM Tris-HCl and 10 mMMgCl2 adjusted to pH 7.5. A sample was taken and analyzed by SDS PAGE: sample in Lane 2, FIG. 11. Impurities in this sample represented about 24% of the sample weight. The diluted sample was filtered through a Vivaspin 2 (Sartorius) 100 kDa membrane from which 200 µL of retentate was obtained. The retentate was then diluted to 2 mL with the same buffer and filtered through the same 100 kDa membrane. Dilution and ultrafiltration of the retentate (200 µL) was repeated four more times. A sample of the retentate was then taken and analyzed by SDS PAGE: sample in Lane 3, FIG. 11. Impurities in this sample represented about 9.7% of the sample weight. In conclusion, the product obtained contained MS2 VLPs with purity higher than 90%.

Example K

Use of Proteinase K (PK) and Simple Precipitation with Ethanol for Purification of VLPs Purification of VLPs was conducted as follows. Samples were taken during purification and SDS PAGE analysis was run on the samples. Results obtained are shown in FIG. 12. One sixth of the pellet obtained from an experiment identical to Example H was resuspended in 20 mM Tris-HCl, pH 7.5, containing 10 mM $MgCl_2$ and sonicated to lyse cells. Cell debris was removed by centrifugation at 16,000 g. The cell lysate obtained was partially purified by precipitation using ammonium sulfate and extraction using trichlorofluoromethane (Freon 11) as described by Strauss & Sinsheimer (1963) J. Mol. Biol 7:43-54. A sample was taken and analyzed: sample in Lane 1, FIG. 12. A strong band at about 14 kDa was found, consistent with the capsid protein of MS2 phage. Other bands—impurities—mostly of higher molecular weight represent about 26% of the sample weight. To the partially purified MS2 VLP solution (1.35 mL) 0.6 mg of Proteinase K dissolved in 1.36 mL of 20 mM $CaCl_2$ aqueous solution was added. The mixture was incubated at 37° C. and after 2.5 hours placed in an ice-water bath. A sample was taken and analyzed by SDS PAGE: sample in Lane 2, FIG. 12. Impurities in this sample represented about 14% of the sample weight. Fifteen minutes afterwards, about 50 µL of 10% acetic acid aqueous solution was added in an ice/water bath to bring the pH of the liquid to 4.1. Then, at the same temperature and with vigorous agitation, 1.54 mL of ethanol was slowly added. The liquid was kept at 0° C. for 30 minutes and centrifuged at 16,000 g at 4° C. for 20 min. The pellet was suspended in 2 mL of an aqueous buffer consisting of 20 mM Tris-HCl and 10 mM $MgCl_2$ adjusted to pH 7.5. A sample was taken and analyzed by SDS PAGE: sample in Lane 3, FIG. 12. Impurities in this sample represented about 10% of the sample weight. The diluted sample was filtered through a Vivaspin 2 (Sartorius) 100 kDa membrane from which 200 µL of retentate was obtained. The retentate was then diluted to 2 mL with the same buffer and filtered through the same 100 kDa membrane. Dilution and ultrafiltration of the retentate (200 µL) was repeated four more times. A sample of the retentate was then taken and analyzed by SDS PAGE: sample in Lane 4, FIG. 12. Impurities in this sample represented about 5.1% of the sample weight. In conclusion, the product obtained contained VLPs with purity of about 95%.

Example L

Use of Constitutive Hydrolases, Fractional Precipitation with Ethanol, and Ultrafiltration for Purification of VLPs Purification of VLPs was conducted as follows. Samples were taken during purification and SDS PAGE analysis was run on the samples. Results obtained are shown in FIG. 13. One sixth of the pellet obtained from an experiment identical to Example H was resuspended in 20 mM Tris-HCl, pH 7.5, containing 10 mM $MgCl_2$ and sonicated to lyse cells. Cell debris was removed by centrifugation at 16,000 g. The cell lysate obtained was partially purified by precipitation using ammonium sulfate and extraction using trichlorofluoromethane (Freon 11) as described by Strauss & Sinsheimer (1963) J. Mol. Biol 7:43-54. To the partially purified VLP solution (1.35 mL) 1.36 mL of 20 mM $CaCl_2$ aqueous solution was added. The mixture was incubated at 37° C. for 2.5 hours (to allow constitutive hydrolases to act) and afterwards was placed in an ice-water bath. A sample was taken and analyzed by SDS PAGE: sample in Lane 1, FIG. 13. Impurities in this sample represented about 12% of the sample weight. Fifteen minutes afterwards, about 120 µL, of 1% sodium hydroxide aqueous solution was added in an ice/water bath to bring the pH of the liquid to 7.86. Then, at the same temperature and with vigorous agitation, 0.81 mL of ethanol was slowly added. The liquid was kept at 0° C. for 30 minutes and centrifuged at 16,000 g at 4° C. for 20 min. About 100 of 10% acetic acid aqueous solution was slowly added to the supernatant with vigorous agitation in an ice/water bath to bring the pH of the liquid to 4.01. Then, at the same temperature and with vigorous agitation, 1.3 mL of ethanol was slowly added. The liquid was kept at 0° C. for 30 minutes and centrifuged at 16,000 g at 4° C. for 20 min. The pellet was suspended in 2 mL of an aqueous buffer consisting of 20 mM Tris-HCl and 10 mM $MgCl_2$ adjusted to pH 7.5. The diluted sample was filtered through a Vivaspin 2 (Sartorius) 100 kDa membrane from which 200 µL of retentate was obtained. The retentate was then diluted to 2 mL with the same buffer and filtered through the same 100 kDa membrane. Dilution and ultrafiltration of the retentate (200 µL) was repeated four more times. A sample of the retentate was then taken and analyzed by SDS PAGE: sample in Lane 3, FIG. 13. Impurities in this sample represented about 4.7% of the sample weight. In conclusion, the product obtained contained VLPs with purity higher than about 95%.

Example M

Use of Proteinase K (PK), Fractional Precipitation with Ethanol, and Ultrafiltration for Purification of VLPs Purification of VLPs was conducted as follows. Samples were taken during purification and SDS PAGE analysis was run on the samples. Results obtained are shown in FIG. 13. One sixth of the pellet obtained from an experiment identical to Example H was resuspended in 20 mM Tris-HCl, pH 7.5, containing 10 mM $MgCl_2$ and sonicated to lyse cells. Cell debris was removed by centrifugation at 16,000 g. The cell lysate obtained was partially purified by precipitation using ammonium sulfate and extraction using trichlorofluoromethane (Freon 11) as described by Strauss & Sinsheimer (1963) J. Mol. Biol 7:43-54. To the partially purified VLP solution (1.35 mL) 0.3 mg of Proteinase K dissolved in 1.36 mL of 20 mM $CaCl_2$ aqueous solution was added. The mixture was incubated at 37° C. for 2.5 hours and afterwards was placed in an ice-water bath. A sample was taken and analyzed by SDS PAGE: sample in Lane 2, FIG. 13. Impurities in this sample represented about 8.1% of the sample weight. Fifteen minutes afterwards, about 120 µL of 1% sodium hydroxide aqueous solution was added in an ice/water bath to bring the pH of the liquid to 7.86. Then, at the same temperature and with vigorous agitation, 0.81 mL of ethanol was slowly added. The liquid was kept at 0° C. for 30 minutes and centrifuged at 16,000 g at 4° C. for 20 min. About 100 µL of 10% acetic acid aqueous solution was added to the supernatant in an ice/water bath to bring the pH of the liquid to 4.0. Then, at the same temperature and with vigorous agitation, 1.3 mL of ethanol was slowly added. The liquid was kept at 0° C. for 30 minutes and centrifuged at 16,000 g at 4° C. for 20 min. The pellet was suspended in 2 mL of an aqueous buffer consisting of 20 mM Tris-HCl and 10 mM $MgCl_2$ adjusted to pH 7.5. The diluted sample was filtered through a Vivaspin 2 (Sartorius) 100 kDa membrane from which 200 µL of retentate was obtained. The retentate was then diluted to 2 mL with the same buffer and filtered through the same 100 kDa membrane. Dilution and ultrafiltration of the retentate (200 µL) was repeated four more times. A sample of the retentate was then taken and analyzed by SDS PAGE: sample in Lane 4, FIG. 13. Impurities in this sample represented about 0.9% of the sample weight. In conclusion, the product obtained contained VLPs with purity higher than about 99%.

Example N

Use of Various Hydrolases, and Factional Precipitation with Ammonium Sulfate for Purification of VLPs Purification of VLPs was conducted as follows. Samples were taken during purification and SDS PAGE analysis was run on the samples. Results obtained are shown in FIG. 14. One sixth of the pellet obtained from an experiment identical to Example H was resuspended in 20 mM Tris-HCl, pH 7.5, containing 10 mM $MgCl_2$ and sonicated to lyse cells. Cell debris was removed by centrifugation at 16,000 g. A sample of the supernatant was taken and analyzed by SDS PAGE: sample in Lane 1, FIG. 14. Impurities in this sample represented about 70% of the sample weight. Four other identical fractions of the pellet obtained from such experiment identical to Example H were processed in the same manner.

The five centrifuged cell lysates obtained, each 3.7 mL in volume, were further processed in five different manners, as follows. The first centrifuged cell lysate was placed in an ice-water bath for 15 minutes and 0.1 grams of ammonium sulfate was added. The mixture was vortexed until complete dissolution of ammonium sulfate was achieved. The liquid was kept at 0° C. for 2 hours and centrifuged at 16,000 g at 4° C. for 30 min. 0.4 grams of ammonium sulfate was added to the supernatant and vortexed until complete dissolution of ammonium sulfate was achieved. The liquid was kept at 0° C. for 2 hours and centrifuged at 16,000 g at 4° C. for 30 min. The purified VLPs pellet was suspended in 0.2 mL of an aqueous buffer consisting of 20 mM Tris-HCl and 10 mM $MgCl_2$ adjusted to pH 7.5. The second centrifuged cell lysate was incubated at 37° C. for five hours, placed in an ice-water bath for the same amount of time as the first centrifuged cell lysate and subsequently processed in identical manner as the first centrifuged cell lysate. One hundred and fifty micrograms of Proteinase K (Sigma Aldrich, St. Louis, Mo.) was added to the third centrifuged cell lysate which was then incubated at 37° C. for five hours, placed in an ice-water bath for the same amount of time as the first centrifuged cell lysate and subsequently processed in identical manner as the first centrifuged cell lysate. The fourth centrifuged cell lysate was incubated at 37° C. for two hours. 0.15 mg of Proteinase K was then added. It was incubated at 37° C. for an additional three hours, placed in an ice-water bath for the same amount of time as the first centrifuged cell lysate and subsequently processed in identical manner as the first centrifuged cell lysate.

Five hundred units of Benzonase® Nuclease (Sigma Aldrich, St. Louis, Mo.) and 35 units of Lipase from *Candida rugosa* (Sigma Aldrich, St. Louis, Mo.) was added to the fifth centrifuged cell lysate and incubated at 37° C. for one hour. 15 units of α-Amylase from *Bacillus* sp. (Sigma Aldrich, St. Louis, Mo.) was then added and incubated at 37° C. for one additional hour. 0.15 mg of Proteinase K was then added. The mixture was incubated at 37° C. for an additional three hours, placed in an ice-water bath for the same amount of time as the first centrifuged cell lysate and subsequently processed in identical manner as the first centrifuged cell lysate.

A sample was taken of the second centrifuged cell lysate after its 5 hours incubation and analyzed by SDS PAGE: sample in Lane 2, FIG. 14. A sample was taken of the third centrifuged cell lysate after its 5 hours incubation and analyzed by SDS PAGE: sample in Lane 3, FIG. 14. A sample was taken of the fourth centrifuged cell lysate after its 5 hours incubation and analyzed by SDS PAGE: sample in Lane 4, FIG. 14. A sample was taken of the fifth centrifuged cell lysate after its 5 hours incubation and analyzed by SDS PAGE: sample in Lane 5, FIG. 14.

A sample was taken of the purified VLPs suspension for the first centrifuged cell lysate and analyzed by SDS PAGE: sample in Lane 6, FIG. 14. The product obtained contained VLPs with purity of about 88%. Protein concentration (Pierce® BCA Protein Assay Kit, Thermo Fisher Scientific, Rockford, Ill.) of this sample was 18.5 mg/mL Optical density measured in a 1 cm cell at 260 nm (OD-260 nm) of a 200:1 dilution of this sample was 0.553 and OD-280 nm was 0.303. These measurements are consistent with RNA yield of about 9 mg per liter of culture.

A sample was taken of the purified VLPs suspension for the second centrifuged cell lysate and analyzed by SDS PAGE: sample in Lane 7, FIG. 14. The product obtained contained VLPs with purity of about 75%. Protein concentration of this sample was 25.4 mg/mL. Optical density measured in a 1 cm cell at 260 nm (OD-260 nm) of a 200:1 dilution of this sample was 0.784 and OD-280 nm was 0.453. These measurements are consistent with RNA yield of about 11 mg per liter of culture.

A sample was taken of the purified VLPs suspension for the third centrifuged cell lysate and analyzed by SDS PAGE: sample in Lane 8, FIG. 14. The product obtained contained VLPs with purity of about 94.3%. Protein concentration of this sample was 21.0 mg/mL. Optical density measured in a 1 cm cell at 260 nm (OD-260 nm) of a 200:1 dilution of this sample was 0.632 and OD-280 nm was 0.321. These measurements are consistent with RNA yield of about 10 mg per liter of culture.

A sample was taken of the purified VLPs suspension for the fourth centrifuged cell lysate and analyzed by SDS PAGE: sample in Lane 9, FIG. 14. The product obtained contained VLPs with purity of about 95.6%. Protein concentration of this sample was 19.4 mg/mL. Optical density measured in a 1 cm cell at 260 nm (OD-260 nm) of a 200:1 dilution of this sample was 0.666 and OD-280 nm was 0.353. These measurements are consistent with RNA yield of about 11 mg per liter of culture.

A sample was taken of the purified VLPs suspension for the fifth centrifuged cell lysate and analyzed by SDS PAGE: sample in Lane 10, FIG. 14. The product obtained contained VLPs with purity of about 96%. Protein concentration of this sample was 19.8 mg/mL Optical density measured in a 1 cm cell at 260 nm (OD-260 nm) of a 200:1 dilution of this sample was 0.661 and OD-280 nm was 0.354. These measurements are consistent with RNA yield of about 11 mg per liter of culture.

Example O

Isolation of RNA Encapsidated in VLPs Obtained in Example N

RNA encapsidated VLPs purified as described in Example N was extracted from each experiment using TRIzol® reagent according to the protocol supplied by the manufacturer (Life Technologies, Grand Island, N.Y.). RNA obtained was denatured by heating for 5 min at 95° C. in formamide and analyzed by electrophoresis in 17.6 cm×38 cm×0.04 cm (W, L, T) gels composed of 8% polyacrylamide, 8 M urea, 1.08% Tris base, 0.55% Boric acid, and 0.093% EDTA. The running buffer had the same concentrations of Tris base, Boric acid and EDTA as the gel. Power was delivered at about 40 W. Gels were stained using a 0.025% solution of Stains-All dye (Sigma-Aldrich, St. Louis, Mo.) in an aqueous mixture containing 25% formamide, 19% isopropanol and 15 mM Tris at pH 8. Results obtained are shown in FIG. 15. Lane numbers for RNA electrophoresis in FIG. 15 refer to the same lane numbers for protein electrophoresis in FIG. 14. A single RNA band can be observed in each lane, consistent with high purity RNA recovered in each case.

Example P

Production of VLPs Using a Transcript Coding for shRNA Against EGFP Flanked by a Long Hammerhead (HH) Ribozyme at its 5' End and Another Long HH Ribozyme Attached to MS2 19-Mer RNA Hairpin at its 3' End Production of MS2 capsids was conducted as follows. The DNA sequence (SEQ ID NO: 5), encoding MS2 capsid protein was cloned into pDEST14 (Life Technologies) plasmid:

Construct T7-Rz4 (SEQ ID NO: 4) encodes a T7 promoter sequence upstream of an shRNA against EGFP flanked by a HH ribozyme designed to cut its 5' end having 12 nucleotides hybridizing to the shRNA and a HH ribozyme designed to cut its 3' end having 23 nucleotides hybridizing to the shRNA was cloned into plasmid pACYC184. A transcription terminator was also cloned at the 3' end of SEQ ID NO: 4 to form pT7-Rz4.

One Shot BL21(DE3) Chemically Competent *E. coli* (Life Technologies) cells were transformed with the two plasmids, one containing MS2 coat protein SEQ ID NO: 5 in pDEST14 and one containing the T7-Rz4 construct SEQ ID NO: 4 in pACYC184, and selecting for chloramphenicol and ampicillin resistant transformants. For capsid production these transformants were grown at 37° C. in 750 mL LB medium containing both ampicillin and chloramphenicol. When the culture density reached OD (600 nm)=0.8, isopropyl β-D-1-thiogalactopyranoside (Sigma-Aldrich) was added to a final concentration of 1 mM. Cells were harvested 4 hours post-induction by centrifugation at 3,000 g and 4° C. for 40 min. A sample was taken prior to induction and at the time of harvest for analysis.

Example Q

Purification of VLPs Obtained in Example P

Purification of VLPs produced in Example P. was conducted as in Example N.

Example R

Isolation of RNA in VLPs Obtained in Example Q

RNA encapsidated in VLPs purified as described in Example Q were extracted using TRIzol® reagent according to the protocol supplied by the manufacturer (Life Technologies, Grand Island, N.Y.). RNA obtained was denatured by heating for 5 min at 95° C. in formamide and analyzed by electrophoresis in Novex® denaturing 15% polyacrylamide TBE-Urea gels (Life Technologies) run at 70° C. RNA bands were visualized using 0.5 μs of Ethidium Bromide (Sigma-Aldrich, St. Louis, Mo.) per mL of aqueous solution. Results obtained are shown in lane 3, FIG. 16. Lane 1 shows a set of molecular standards. Lane 2 shows a chemically synthesized shRNA 49 nucleotides long.

Example S

VLPs Obtained in Example Q are Resistant to Proteinase K from *Engyodontium Album*, Protease from *Bacillus Licheniformis*, Pepsin from Porcine Gastric Mucosa, and Papain from Papaya Latex VLPs obtained from 250 mL of culture and purified as described in Example-Q were suspended in 400 μL 20 mM $CaCl_2$ aqueous solution at pH=7.5.

A 66 μL aliquote of this suspension was diluted to 0.25 mL with 20 mM $CaCl_2$ aqueous solution at pH=7.5 and incubated at 37° C. Samples were taken for protein concentration (Pierce® BCA Protein Assay Kit, Thermo Fisher Scientific, Rockford, Ill.) and SDS PAGE analyses after 1 hour, and 4 hours of incubation. Protein concentration in these 2 samples was 3,086, and 4,656 mg/L respectively. SDS PAGE analyses are shown in FIG. 17, Lanes IB, and 6 respectively. The same amount of protein was loaded in each lane (4 μg). This set of experiments was used as a negative control. Two μg Protease from *Streptomyces griseus* (Sigma Aldrich, St. Louis, Mo.) was diluted to 0.25 mL with 20 mM $CaCl_2$ aqueous solution at pH=7.5 and incubated at 37° C. Samples were taken for protein concentration and SDS PAGE analyses after 1 hour, and 4 hours of incubation. Protein concentration in these 2 samples was 361 and 324 mg/L respectively. SDS PAGE analyses are shown in FIG. 17, Lanes 1, and 7 respectively. The same amount of protein was loaded in each lane (4 μg). This set of experiments was used as another negative control.

Two μg of Protease from *Streptomyces griseus* was added to another 66 μL aliquote of the VLPs comprising MS2 capsids suspension, diluted to 0.25 mL with 20 mM $CaCl_2$ aqueous solution at pH=7.5 and incubated at 37° C. Samples were taken for protein concentration and SDS PAGE analyses after 1 hour, and 4 hours of incubation. Protein concentration in these 2 samples was 2,940, and 3,012 mg/L respectively. SDS PAGE analyses are shown in FIG. 17, Lanes 2, and 8 respectively. The same amount of protein was loaded in each lane (4 μg). This set of experiments was used to test the proteolytic stability towards Protease from *Streptomyces griseus* of MS2 capsids forming the VLPs. Less than 10% degradation was observed.

Another 66 aliquote of the VLPs comprising MS2 capsids suspension, diluted to 0.25 mL with 20 mM $CaCl_2$ aqueous solution at pH=7.5 was subjected to three cycles of heating to 95° C. for 10 minutes and cooling on wet ice for 10 min to achieve the disassembly of the VLPs. Two µg of Protease from *Streptomyces griseus* was then added to this suspension and was incubated at 37° C. Samples were taken for protein concentration and SDS PAGE analyses after 1 hour, and 4 hours of incubation. Protein concentration in these 2 samples was 2,601, and 3,033 mg/L respectively. SDS PAGE analyses are shown in FIG. 17, Lanes 3, and 9 respectively. The same amount of protein was loaded in each lane (4 µg). Disassembled particles were degraded to a significant extent by Protease from *Streptomyces griseus*. This set of experiments was used as a positive control.

Two µg of Protease from *Streptomyces griseus* dissolved in 0.002 mL of 20 mM $CaCl_2$ aqueous solution at pH=7.5 was added to 0.248 mL of bacterial cell lysate obtained from 41 mL of cell culture from example P and incubated at 37° C. Samples were taken for protein concentration and SDS PAGE analyses after 1 hour, and 4 hours of incubation. Protein concentration in these 2 samples was 3,192, and 4,837 mg/L respectively. SDS PAGE analyses are shown in FIG. 17, Lanes 4, and 10 respectively. The last lane of FIG. 17, labeled L, shows untreated bacterial cell lysate. The same amount of protein was loaded in each lane (4 µg). More than 90% of proteins other than MS2 capsid protein were degraded by Protease from *Streptomyces griseus*. This set of experiments was used as another positive control.

This set of five experiments demonstrate that MS2 capsids form VLPs resistant to proteolysis by Protease from *Streptomyces griseus*.

Two µg Protease from *Bacillus licheniformis* (Sigma Aldrich, St. Louis, Mo.) was diluted to 0.25 mL with 10 mM Na acetate and 5 mM Ca acetate aqueous solution at pH=7.5 and incubated at 37° C. Samples were taken for protein concentration and SDS PAGE analyses after 1 hour, and 4 hours of incubation. Protein concentration in these 2 samples was 976, and 1,003 mg/L respectively. SDS PAGE analyses are shown in FIG. 17, Lanes 2B, and 7B respectively.

The same amount of protein was loaded in each lane (4 µg). This set of experiments was used as another negative control.

Two µg of Protease from *Bacillus licheniformis* was added to another 66 µL, aliquote of the VLPs comprising MS2 capsids suspension, diluted to 0.25 mL with 10 mM Na acetate and 5 mM Ca acetate aqueous solution at pH=7.5 and incubated at 37° C. Samples were taken for protein concentration and SDS PAGE analyses after 1 hour, and 4 hours of incubation. Protein concentration in these 2 samples was 3,144, and 3,727 mg/L respectively. SDS PAGE analyses are shown in FIG. 17, Lanes 3B, and 8B respectively. The same amount of protein was loaded in each lane (4 µg). This set of experiments was used to test the proteolytic stability towards Protease from *Bacillus licheniformis* of MS2 capsids forming the VLPs. Less than 10% degradation was observed.

Another 66 µL aliquote of the VLPs comprising MS2 capsids suspension, diluted to 0.25 mL with 10 mM Na acetate and 5 mM Ca acetate aqueous solution at pH=7.5 was subjected to three cycles of heating to 95° C. for 10 minutes and cooling on wet ice for 10 min to achieve the disassembly of the VLPs. Two µg of Protease from *Bacillus licheniformis* was then added to this suspension and was incubated at 37° C. Samples were taken for protein concentration and SDS PAGE analyses after 1 hour, and 4 hours of incubation. Protein concentration in these 2 samples was 1,769, and 1,785 mg/L respectively. SDS PAGE analyses are shown in FIG. 17, Lanes 4B, and 9B respectively. The same amount of protein was loaded in each lane (4 µg). Disassembled particles were degraded by Protease from *Bacillus licheniformis*. This set of experiments was used as a positive control.

Two µg of Protease from *Bacillus licheniformis* dissolved in 0.002 mL of 10 mM Na acetate and 5 mM Ca acetate aqueous solution at pH=7.5 was added to 0.248 mL of bacterial cell lysate obtained from 41 mL of cell culture from example P and incubated at 37° C. Samples were taken for protein concentration and SDS PAGE analyses after 1 hour, and 4 hours of incubation. Protein concentration in these 2 samples was 3,696, and 4,078 mg/L respectively. SDS PAGE analyses are shown in FIG. 17, Lanes 6B, and 10B respectively. The last lane of FIG. 17, labeled L, shows untreated bacterial cell lysate. The same amount of protein was loaded in each lane (4 µg). More than 90% of proteins other than MS2 capsid protein were degraded by Protease from *Bacillus licheniformis*. This set of experiments was used as another positive control.

This set of four experiments demonstrated that MS2 capsid proteins in VLPs are resistant to proteolysis by Protease from *Bacillus licheniformis*.

Three additional sets of equivalent experiments demonstrated that MS2 capsid proteins in VLPs are resistant to proteolysis by any of the following three proteases: Proteinase K from *Engyodontium album*, Pepsin from porcine gastric mucosa (CAS Number 9001-75-6), and Papain from papaya latex (CAS Number 9001-73-4) (Sigma-Aldrich, St. Louis, Mo.). Each protease was used according the manufacturer's instructions. Proteinase K was used at pH=7.5, Pepsin was used at pH=1.6, and Papain was used at pH=6.6.

The invention claimed is:

1. A process for purifying a quantity of virus-like particles (VLPs) consisting of Enterobacteriophage MS2 capsid proteins (SEQ ID NO.: 3) enclosing at least one heterologous cargo molecule, the process comprising: (a) obtaining a cell lysate comprising a plurality of the VLPs; (b) contacting the cell lysate with a protease for a time and under conditions sufficient to hydrolyze cell lysis products other than the VLPs to form a hydrolysate; and (c) isolating the VLPs from the hydrolysate.

2. The process according to claim 1, wherein the protease is a peptide bond hydrolase category E.C. 3.4.

3. The process according to claim 1, wherein the protease is selected from Proteinase K, Protease from *Streptomyces griseus*, Protease from *Bacillus licheniformis*, pepsin and papain.

4. The process according to claim 1, wherein step (b) is performed for about 30 minutes.

5. The process according to claim 1, wherein step (b) is performed at about 37° C.

6. The process according to claim 1, wherein the time and condition for hydrolysis are sufficient for at least 60, at least 70, at least 80, or at least 90 of every 100 individual polypeptides present in the whole cell lysate but not enclosed by the capsids to be cleaved, while at least 60, at least 70, at least 80, or at least 90 of every 100 capsids present in the whole cell lysate before such hydrolysis remain intact following the hydrolysis.

7. The process according to claim 1, wherein step (b) further comprises, contacting the cell lysate with at least one of the group consisting of a nuclease, an amylase and a lipase.

8. The process according to claim 1, wherein step (c) comprises centrifuging the hydrolysate to obtain a precipitate comprising at least 90% by weight of the VLPs.

9. The process according to claim 1, wherein step (c) comprises (i) performing a first precipitation of the hydrolysate with ammonium sulfate followed by a first centrifugation to obtain a first precipitate and a first supernatant; and (ii) performing a second precipitation on the first supernatant with ammonium sulfate followed by a second centrifugation to obtain a second precipitate, wherein the second precipitate comprises at least 90% by weight of the VLPs.

10. The process according to claim 1, wherein step (c) comprises (i) performing a first precipitation of the hydrolysate with ethanol followed by a first centrifugation to obtain a first precipitate and a first supernatant; and (ii) performing a second precipitation on the first supernatant with ammonium sulfate followed by a second centrifugation to obtain a second precipitate, wherein the second precipitate comprises at least 90% by weight of the VLPs.

11. The process according to claim 1, wherein the heterologous cargo molecule comprises an oligonucleotide linker coupling the heterologous cargo molecule and the VLP.

12. The process according to claim 11, wherein the oligonucleotide linker is an oligoribonucleotide.

13. The process according to claim 1, wherein the heterologous cargo molecule comprises an oligoribonucleotide selected from siRNA, shRNA, sshRNA, lshRNA and miRNA.

14. The process according to claim 1, wherein the heterologous cargo molecule comprises an oligoribonucleotide comprising a ribozyme.

15. The process according to claim 1, wherein the heterologous cargo molecule comprises a peptide or a polypeptide.

16. The process according to claim 1, wherein the VLPs isolated from the hydrolsate comprise less than 4 grams of one or more cell lysis products for every 100 grams of capsid present in the composition, wherein the cell lysis products are selected from proteins, polypeptides, peptides and any combination thereof.

17. The process of claim 1, wherein the quantity of virus-like particles (VLPs) enclosing at least one heterologous cargo molecule is at least ten milligrams.

18. The process of claim 1, wherein the quantity of virus-like particles (VLPs) enclosing at least one heterologous cargo molecule is at least one gram.

19. The process of claim 1, wherein the quantity of virus-like particles (VLPs) enclosing at least one heterologous cargo molecule is at least one hundred grams.

* * * * *